US009775776B2

(12) United States Patent
Morimoto et al.

(10) Patent No.: US 9,775,776 B2
(45) Date of Patent: Oct. 3, 2017

(54) MEDICATION STORAGE CELL

(71) Applicant: MORIMOTO-PHARMA CO., LTD., Osaka-shi, Osaka (JP)

(72) Inventors: Shuji Morimoto, Osaka (JP); Masao Nozaki, Osaka (JP)

(73) Assignee: MORIMOTO-PHARMA CO., LTD., Osaka-shi, Osaka (JP)

(*) Notice: Subject to any disclaimer, the term of this patent is extended or adjusted under 35 U.S.C. 154(b) by 0 days.

(21) Appl. No.: 15/222,885

(22) Filed: Jul. 28, 2016

(65) Prior Publication Data

US 2016/0331634 A1 Nov. 17, 2016

Related U.S. Application Data

(63) Continuation of application No. PCT/JP2015/052400, filed on Jan. 28, 2015.

(51) Int. Cl.
*B65D 1/09* (2006.01)
*A61J 1/03* (2006.01)
(Continued)

(52) U.S. Cl.
CPC ................ *A61J 1/035* (2013.01); *A61J 1/03* (2013.01); *B65D 75/28* (2013.01); *B65D 75/366* (2013.01)

(58) Field of Classification Search
CPC ...... B65D 85/60; B65D 71/06; B65D 71/063; B65D 71/066; B65D 75/40; B65D 75/42;
(Continued)

(56) References Cited

U.S. PATENT DOCUMENTS 3,214,013 A * 10/1965 Diamant ................ B65D 75/30 206/484
3,478,871 A * 11/1969 Sager ................ B65D 81/3266 206/221

(Continued)

FOREIGN PATENT DOCUMENTS

JP 2002-205767 A 7/2002
JP 2002-248156 A 9/2002

(Continued)

OTHER PUBLICATIONS

International Search Report for PCT/JP2015/052400 dated Apr. 28, 2015.

(Continued)

*Primary Examiner* — Steven A. Reynolds
*Assistant Examiner* — Javier A Pagan
(74) *Attorney, Agent, or Firm* — Yokoi & Co., U.S.A.; Toshiyuki Yokoi

(57) ABSTRACT

To provide a medication storage cell that can be easily opened by a person who cannot dexterously move his or her fingertips. A small-medication storage cell (12) is provided with an accommodating section (20) and an interlocking piece (22). The accommodating section (20) has an outlet for a medication (100). The outlet (30) is formed using a sheet (60) provided with an interlocking piece, and a cover sheet (62). The interlocking piece (22) has a base section (40) and a tip end section (42). At least a part of the base section (40) is separated from the surface of the accommodating section (20). The tip end section (42) is fastened to the accommodating section (20) in a bent state so that the cover sheet (62) and the sheet (60) provided with an interlocking piece close the outlet (30).

5 Claims, 15 Drawing Sheets

(51) Int. Cl.
*B65D 75/28* (2006.01)
*B65D 75/36* (2006.01)

(58) Field of Classification Search
CPC ........ B65D 75/44; B65D 75/46; B65D 75/48; B65D 75/527; B65D 75/5888
USPC .... 206/528, 531, 532, 539, 484.2, 484, 828, 206/223
See application file for complete search history.

(56) References Cited

U.S. PATENT DOCUMENTS

| | | | | | |
|---|---|---|---|---|---|
| 3,958,750 | A | * | 5/1976 | Prybeck | B65D 31/12 206/260 |
| 4,706,297 | A | * | 11/1987 | Ausnit | B65D 33/2566 383/122 |
| 5,325,968 | A | * | 7/1994 | Sowden | A61J 1/035 206/532 |
| 5,358,118 | A | * | 10/1994 | Thompson | A61J 1/035 206/538 |
| D364,086 | S | * | 11/1995 | Jacobson | D9/705 |
| 5,715,943 | A | * | 2/1998 | Thompson, Jr. | A61L 2/26 206/363 |
| 5,775,489 | A | * | 7/1998 | Vickers | B65D 5/4802 206/307.1 |
| 6,845,883 | B2 | * | 1/2005 | Pieri | B65D 75/527 222/541.6 |
| 7,210,580 | B2 | * | 5/2007 | Elliott | B65D 75/327 206/528 |
| 2013/0015085 | A1 | * | 1/2013 | Morimoto | A61J 7/0046 206/219 |

FOREIGN PATENT DOCUMENTS

| | | | |
|---|---|---|---|
| JP | 2004-018081 | A | 1/2004 |
| JP | 2008-037460 | A | 2/2008 |

OTHER PUBLICATIONS

PCT written opinion dated Apr. 28, 2015.
Japanese decision to grant a patent dated Sep. 1, 2015.
Japanese notice of the reason for refusal dated May 26, 2015.

* cited by examiner

MEDICATION STORAGE CELL

CROSS-REFERENCES TO RELATED APPLICATIONS

This application claims the benefit of priority and is a Continuation application of the prior International Patent Application No. PCT/JP2015/052400, with an international filing date of Jan. 28, 2015, which designated the United States, and is related to the International Patent Application No. PCT/JP2014/051918, filed Jan. 29, 2014, the entire disclosures of all applications are expressly incorporated by reference in their entirety herein.

BACKGROUND OF THE INVENTION

1. Field of the Invention

This invention is related to a medication storage cell, a strip packaging body, and a method for manufacturing the medication storage cell, and more specifically, related to the medication storage cell and the strip packaging body that can be easily opened by persons who have difficulty in moving their fingertips dexterously, and the method for manufacturing the medication storage cell.

2. Description of Related Art

Patent document 1 discloses a solid formulation packaging body. This is provided with an accommodating section to accommodate the solid formulation and a seal section to seal the edges of the accommodating section. The seal section has at least one region with a weak seal section that can be opened. The weak seal section is of a length that can form an opening. The solid formulation from the accommodating section can be passed through the opening. The accommodating section is formed using flexible packaging material. The flexible packaging material allows the solid formulation inside the accommodating section to be held using fingers. The flexible packaging material has one or more plastic layers. The solid formulation packaging body disclosed in patent document 1 can be easily opened by persons who do not have the strength in their fingertips and those who can use only one hand.

Patent document 1: Japanese Published Unexamined Application No. 2002-205767

BRIEF SUMMARY OF THE INVENTION

The solid formulation packaging body disclosed in patent document 1 has a problem that the packaging body cannot be easily opened by persons who cannot move their fingertips dexterously.

This invention was made to solve the above-mentioned technical problem, and the objective is to provide a medication storage cell and a strip packaging body that can be easily opened by persons who have difficulty in moving their fingertips dexterously, and a method for manufacturing the medication storage cell.

The medication storage cell, the strip packaging body, and the method for manufacturing the medication storage cell of this invention will be explained using the drawings. Moreover, symbols from the drawings used in this section are to help in understanding the contents of the invention and are not intended to limit the invention to the scope of the drawings.

To achieve the above object, according to this invention, a medication storage cell 12, 14, 18, 312, 314 provides an accommodating section 20, 320 that accommodates a medication 100. The accommodating section 20, 320 has an outlet 30, 330 for the medication 100. The outlet 30, 330 is formed by overlapping sheets 60, 62, 360, 362. The overlapping sheets 60, 62, 360, 362 are bent such that the outlet 30, 330 is closed.

If the overlapping sheets 60, 62, 360, 362 are bent such that the outlet 30, 330 is closed, then the adhesive strength between the overlapping sheets 60, 62, 360, 362 can be lowered even if the overlapping sheets 60, 62, 360, 362 are assumed to be stuck. The overlapping sheets 60, 62, 360, 362 need not be stuck between them. With this, the outlet 30, 330 can be easily opened even by persons who cannot move their fingertips dexterously.

Also, the medication storage cell 12, 14, 18, 312, 314 described above provides a sheet restraining section along with the accommodating section 20, 320. The sheet restraining section restrains a part of the overlapping sheets 60, 62, 360, 362 to maintain the bent state such that the outlet 30, 330 is closed.

When the sheet restraining section restrains a part of the overlapping sheets 60, 62, 360, 362, the possibility of opening the outlet 30, 330 is lowered when compared to the condition with no restraint. On the other hand, only a part of the overlapping sheets 60, 62, 360, 362 is restrained by the sheet restraining section, and the other parts are not restrained by the sheet restraining section. With this, the restraint state is easy to release compared to the case where the entire section of the overlapping sheets 60, 62, 360, 362 are restrained. Since the restraint state can be easily released, the bent state such that the outlet 30, 330 is closed can be easily released compared to the case where the entire overlapping sheets 60, 62, 360, 362 are restrained. As a result, the possibility of opening the outlet 30, 330 until the restraint of the sheet restraining section has been released is low, and the outlet 30, 330 can be easily opened even by persons who cannot move their fingertips dexterously.

The sheet restraining section described above has an interlocking piece 22. The interlocking piece 22 is provided integrally with one side 60 of the overlapping sheets 60, 62. In this case, the interlocking piece 22 has a base section 40 and a tip end section 42. The base section 40 is provided such that it is continuous with the edges of outlet 30. The tip end section 42 is continuous with the base section 40. At least a part of the base section 40 is separated from the surface of the accommodating section 20. The accommodating section 20 has a mutually bonded structure around the medication 100 of the two sheets 60, 62 accommodating the medication 100 between them. The tip section 42 is held at the location of the accommodating section 20 where the one side 60 of the two sheets 60, 62 is not covered by the other side 62, at the edge of the accommodating section 20 on the opposite side of the outlet 30 when viewed from the medication 100 in the state where the overlapping sheets 60, 62 are bent such that the outlet 30 is closed.

At least a part of the base section 40 of interlocking piece 22 is separated from the surface of the accommodating section 20. The tip section 42 of the interlocking piece 22 is held at the location where the one side 60 of the two sheets 60, 62 is not covered by the other side 62, at the edge of the accommodating section 20 on the opposite side of the outlet 30 when viewed from the medication 100 in the state where the overlapping sheets 60, 62 are bent such that the outlet 30 is closed. The tip section 42 of the interlocking piece 22 can be separated from the accommodating section 20 by inserting objects such as a person's finger at places where the base section 40 of the interlocking piece 22 is separated from the surface of the accommodating section 20. If the tip section 42 of the interlocking piece 22 is separated from the accommodating section 20 and the overlapping sheets 60, 62 that forms the outlet 30 are straightened from the bent state, then the medication 100 can be removed from the accommodating section 20 through the outlet 30. If the tip end section 42 of the interlocking piece 22 is held at the accommodating section 20, then the movement of the interlocking piece 22 will be restrained until the tip end section 42 is separated. If the movement of the interlocking piece 22 is restrained, then the movement of the overlapping sheets 60, 62 will also be restrained. Since the movement of the overlapping sheets 60, 62 is restrained, opening of the outlet 30 will be prevented until the tip end section 42 of the interlocking piece 22 is separated from the accommodating section 20. On the other hand, if the tip section 42 of the interlocking piece 22 is separated from the accommodating section 20, then the restraint of the overlapping sheets 60, 62 will be released. The outlet 30 can be opened as the restraint is released. With this, the outlet 30 can be opened by inserting objects such as a person's finger at places where the base section 40 of the interlocking piece 22 is separated from the surface of the accommodating section 20. As a result, the outlet 30 can be easily opened even by persons who cannot move their fingertips dexterously.

Also, the sheet restraining section described above has an interlocking piece 322. The interlocking piece 322 is provided on one side 360 of the overlapping sheets 360, 362. The interlocking piece 322 is held through the cut out 340 at the accommodating section 320 in the state where the overlapping sheets 360, 362 are bent such that the outlet 330 is closed. The cut out 340 is provided on the other side 362 of the overlapping sheets 360, 362. The interlocking piece 322 that is held through the cut out 340 at the accommodating section 320 can be separated from the accommodating section 320 by inserting objects such as a person's finger between the interlocking piece 322 and the accommodating section 320, and the medication 100 can be removed from the accommodating section 320 through the outlet 330 by straightening the overlapping sheets 360, 362 from its bent state. With this, same as above, the packaging can be easily opened even by persons who cannot move their fingertips dexterously.

Also, it is preferable that the overlapping sheets 60, 62, 360, 362 which form the outlet 30, 330 described above are mutually pasted together such that the outlet 30, 330 is closed. In this case, it is preferable that the bent locations 52, 354 of the overlapping sheets 60, 62, 360, 362 is arranged on the side where the medication 100 is present when viewed from the mutually pasted region 32, 332 or in the mutually pasted region 32, 332.

Since the bent locations 52, 354 of the overlapping sheets 60, 62, 360, 362 is arranged on the side where the medication 100 is present when viewed from the mutually pasted region 32, 332 or in the mutually pasted region 32, 332, the outlet 30, 330 will be closed by the sheets 60, 62, 360, 362 which are overlapping and bent and the mutually pasted region 32, 332. If the overlapping sheets 60, 62, 360, 362 forming the outlet 30, 330 are mutually pasted together, the overlapping sheets 60, 62, 360, 362 combined with bent such that the outlet 30, 330 is closed enable the outlet 30, 330 to be closed firmly when the tip end section 42 of the interlocking piece 22, 322 is held at the accommodating section 20. Since closing firmly is possible, the adhesive strength between the overlapping sheets 60, 62, 360, 362 can be lowered when compared to the case where the outlet 30, 330 is sealed by the overlapping sheets 60, 62, 360, 362 just mutual pasting without bending to close the outlet 30, 330. Since the adhesive strength can be lowered, opening of the outlet 30, 330 is easy even for persons who cannot move their fingertips dexterously, in addition, sealing is possible similar to the case where the outlet 30, 330 is sealed by the overlapping sheets 60, 62, 360, 362 just mutual pasting.

Also, it is preferable that the accommodating section 320 described above has a limiting section 342 in addition to the outlet 330. The limiting section 342 restricts the movable range of the medication 100 within the accommodating section 320.

The limiting section 342 restricts the movable range of the medication 100 within the accommodating section 320, and prevents the medication 100 from moving to the rear of the accommodating section 320 compared to the case where such a restriction is not provided. Removing the medication 100 from the accommodating section 320 becomes easy in case where the movement of the medication 100 to the rear of the accommodating section 320 is prevented compared to the case where such a restriction is not provided.

Also, it is preferable that the friction coefficient of the inner surface of the accommodating section 320 described above that is in contact with the medication 100 is lower than the friction coefficient of the outer surface.

Since the coefficient of friction of the outer surface is higher than that of the inner surface, when the medication 100 is removed from the accommodating section 320, the medication slides more easily on the inner surface of the accommodating section 320 compared to the outer surface of the accommodating section 320. Since the inner surface of the accommodating section 320 is more slippery than the outer surface, the medication 100 can be easily removed by a person who cannot apply sufficient force to an object.

Also, it is preferable that the accommodating section 320 described above has an outer edge section 376 with a curved contour in addition to the outlet 330.

The outer edge section 376 having a curved contour is less likely to cause damage to the human body when compared to the contour with acute or right angle sections. With this, when the accommodating section 320 has the outer edge section 376 having a curved contour, compared to the case without this, the outer edge section 376 of the accommodating section 320 is less likely to damage the human body. Specifically, the possibility of the outer edge section 376 of the accommodating section 320 damaging the internal organs of the person when the medication storage cell 12, 14 is swallowed by mistake is reduced.

According to another aspect of this invention, the strip packaging body 10, 310 is provided with multiple numbers of the medication storage cell 12, 14, 312, 314. The medication storage cell 12, 14, 312, 314 are lined up such that rows 70, 72 are configured. The medication storage cell 12, 14, 312, 314 has the accommodating section 20, 320. The accommodating section 20, 320 stores the medication 100. The accommodating section 20, 320 has an outlet 30, 330 for the medication 100. The outlet 30, 330 is formed by the overlapping sheets 60, 62. The overlapping sheets 60, 62, 360, 362 are bent such that the outlet 30, 330 is closed.

The individual medication storage cell 12, 14, 312, 314 can be easily opened even by persons who cannot move their fingertips dexterously.

Also, it is preferable that multiple medication storage cells 12, 14 described above are lined up such that multiple rows 70, 72 are configured. In this case, it is preferable that the strip packaging body 10 has a bending section between rows 16 in addition to the multiple rows 70, 72. The bending section between rows 16 is provided between the rows 70, 72. In this case, it is preferable that the medication storage cell 12, 14 is provided with the interlocking piece 22 in addition to the accommodating section 20. The interlocking piece 22 is provided on one side of the overlapping sheets 60, 62. The interlocking piece 22 has a base section 40 and a tip end section 42. The base section 40 is provided such that it is continuous with the edges of outlet 30. The tip end section 42 is continuous with the base section 40. At least a part of the base section 40 is separated from the surface of the accommodating section 20. The tip end section 42 is held at the accommodating section 20 in the state where the overlapping sheets 60, 62 are bent such that the outlet 30 is closed. In this case, it is preferable that the medication storage cell 12 configuring any one 70 of the multiple rows overlaps any one 72 of another row when the bending section between rows 16 is bent. It is preferable that the medication storage cell 12 configuring any one 70 of the multiple rows is in a state shifted relative to the medication storage cell 14 configuring another row 72.

If the medication storage cell 12 configuring any one 70 of the multiple rows is in a state shifted relative to the medication storage cell 14 configuring another row 72, compared to the case where there is no such shift, the medication 100 in the medication storage cell 12 configuring any one 70 of the multiple rows is likely to be in the shifted state relative to the medication 100 in the medication storage cell 14 configuring another one 72 of the multiple rows. When the shift between the medication 100 to each other occurs, compared to the case without the shift, the strip packaging body 10 in the state that the medication storage cell 12 configuring any one 70 of the multiple rows overlaps with any one of another row 72 will be thinner. If the strip packaging body 10 is thinner, the space required for storage is reduced.

Also, it is preferable that the strip packaging body 310 described above has a connecting section 316 at least at one location in addition to the multiple numbers of medication storage cell 312, 314. The connecting section 316 is arranged between multiple numbers of the medication storage cell 312, 314. The connecting section 316 connects the medication storage cells 312, 314 to each other. In this case, it is preferable if any one of the connecting section 316 at least at one location can be bent such that the medication storage cells 312, 314 face each other.

According to another aspect of this invention, a manufacturing method of the medication storage cell is the manufacturing method of the medication storage cell 12, 14, 18, 312, 314. The medication storage cell 12, 14, 18, 312, 314 uses sheet 110, 112, 510, 512 as material. The medication 100 is accommodated in the medication storage cell 12, 14, 18, 312, 314. The manufacturing method of the medication storage cell comprises of an accommodation bonding process S200, S600 and a bending process S206, S606. The medication 100 is accommodated between the overlapping sheets 110, 112, 510, 512 in the accommodation bonding process S200, S600. A surrounding region 32, 34, 36, 332, 334, 336 is bonded in the accommodation bonding process S200 such that the outlet 30, 330 for the medication 100 is formed. The surrounding region 32, 34, 36, 332, 334, 336 is the region around the medication 100 between the overlapping sheets 110, 112, 510, 512. The bend location 52, 354 is bent with the bending process S206, S606. The bending location 52, 354 is formed at predetermined locations of the overlapping sheets 110, 112, 510, 512. The bending location 52, 354 is in the direction with the outlet 30, 330 when viewed from the medication 100.

Also, the overlapping sheets 110, 112 described above has an interlocking piece forming sheet 110 and a cover forming body 112. The cover forming body 112 covers a part of the interlocking piece forming sheet 110. In this case, the bending process S206 has the following process. That is the process in which the bending location 52 is bent such that the interlocking part 160 faces the part of the interlocking piece forming sheet 110 that is at the opposite side of the interlocking part 160 when viewed from the medication 100 and is not covered by the cover forming body 112. The interlocking part 160 is the part of the interlocking piece forming sheet 110 that is not covered by the cover forming body 112 at the side with the outlet 30 when viewed from the medication 100. In this case, the manufacturing method of the medication storage cell further comprises of a facing location hold process S208. In the facing location hold process S208, any one of the locations of the interlocking part 160 is held at the facing location in the bending process S206.

Also, a cut out is formed on one side 512 of the overlapping sheets described above. In this case, the bending process S606 has the following process. That is the process in which the bending location 354 is bent such that the interlocking part faces any of the locations other than the interlocking part of the other side 510 of the overlapping sheets through the cut out of one side 512 of the overlapping sheets. The interlocking part is any part of the other side 510 of the overlapping sheets that is not covered by the one side 512 of the overlapping sheet. In this case, the manufacturing method of the medication storage cell 312, 314 further comprises of a facing location hold process S608. In the facing location hold process S608, the interlocking part is held at the location facing through the cut out in the other side 510 of the overlapping sheets.

Effect of the Invention

According to this invention, the medication storage cell can be easily opened by persons who cannot move their fingertips dexterously.

DETAILED DESCRIPTION OF THE INVENTION

Embodiment 1

In the following, embodiment 1 of this invention is explained with reference to the drawings. In the following explanation, the same components are denoted using the same symbols. Their names and functions are also the same. Therefore, their detailed explanation will not be repeated.

[Explanation of the Structure]

Figure 1:
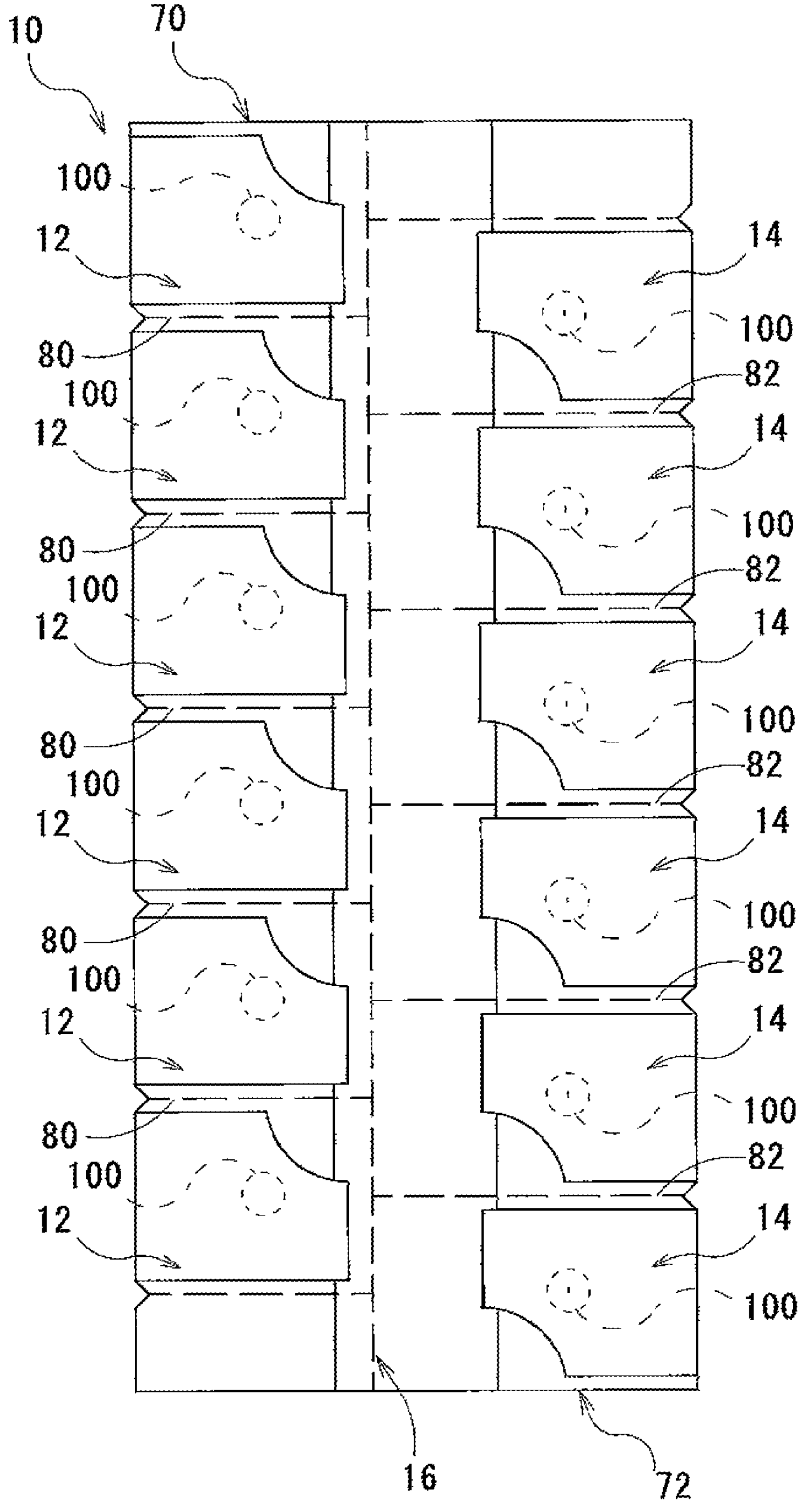
FIG. 1 Plan view of the strip packaging body related to embodiment 1 of this invention.

FIG. 1 is the plan view of the strip packaging body 10 related to this embodiment. The strip packaging body 10 related to this embodiment is explained in reference to FIG. 1. The strip packaging body 10 related to this embodiment is provided with multiple numbers of small medication storage cell 12, and multiple numbers of large medication storage cell 14 and bending section between rows 16.

Each of the small medication storage cell 12 and the large medication storage cell 14 accommodates a medication 100. As apparent from FIG. 1, the small medication storage cell 12 is lined up to configure the first row 70. The large medication storage cell 14 is lined up to configure the second row 72. Except for the point described below, the structure of the small medication storage cell 12 and the structure of the large medication storage cell 14 is the same. The point, as shown in FIG. 1 is, the length of the small medication storage cell 12 in the width direction for the first row 70 is less than the length of the large medication storage cell 14 in the width direction for the second row 72.

The "medication" in this embodiment refers to the solid that can be dosed by either humans or animals. There is no particular limit on the size of the medication 100 as long as the solid can be dosed by either humans or animals. Therefore, the medication 100 can be either in powder or mass form. As long as the solid can be dosed by either humans or animals, the medication 100 may or may not be a poison to humans or animals. For example, the medication can be food such as confectionery. Note that, the medication 100 shown in FIG. 1 is in the form of known tablets.

The bending section between rows 16 is provided between the first row 70 and the second row 72. As described above, the length of the small medication storage cell 12 in the width direction for the first row 70 is less than the length of the large medication storage cell 14 in the width direction for the second row 72. Accordingly, the position of the bending section between rows 16 is offset from the center of the strip packaging body 10 in the strip packaging body 10 related to this embodiment. In this embodiment, perforations are provided in the bending section between rows 16. With this, the strip packaging body 10 related to this embodiment can be bent at the bending section between rows 16. Also, the first row 70 and the second row 72 can be easily cut-off.

Figure 2:
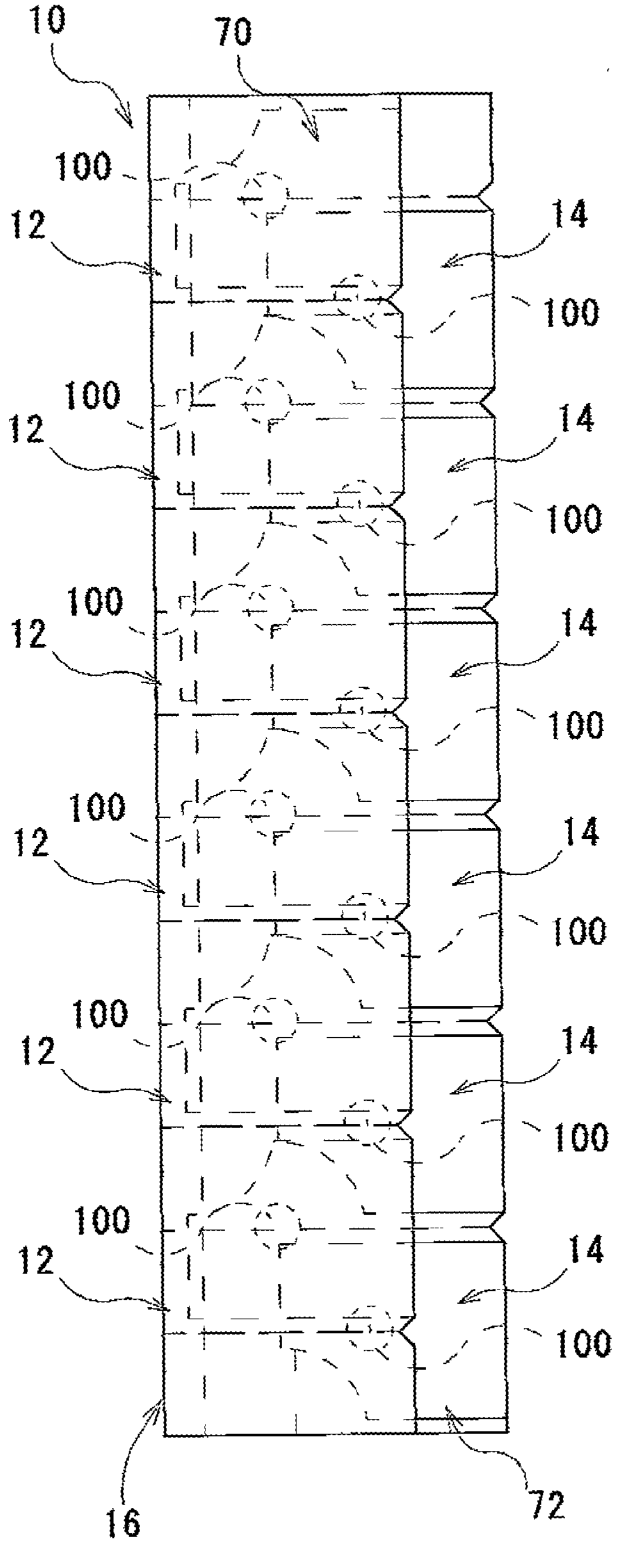
FIG. 2 Plan view showing the state of the strip packaging body folded into two related to embodiment 1 of this invention.

In this embodiment, perforations are provided at the boundary section 80 between two numbers of the small medication storage cell 12 in the first row 70. Perforations are provided at the boundary section 82 between two numbers of the large medication storage cell 14 even in the second row 72. With this, it is possible to cut-off the two numbers of the small medication storage cell 12 easily. The two numbers of the large medication storage cell 14 can be easily cut-off. FIG. 2 is the plan view showing the state of the strip packaging body 10 folded into two related to this embodiment. As apparent from FIG. 2, in this embodiment, the small medication storage cell 12 configuring the first row 70 is lined up facing respectively between two numbers of the large medication storage cell 14 configuring the second row 72 when the strip packaging body 10 is bent along the bending section between rows 16. The large medication storage cell 14 configuring the second row 72 is lined up facing respectively between two numbers of the small medication storage cell 12 configuring the first row 70 when the strip packaging body 10 is bent along the bending section between rows 16. Moreover, as shown in FIG. 1, and as explained above, the length of the small medication storage cell 12 in the width direction for the first row 70 is less than the length of the large medication storage cell 14 in the width direction for the second row 72. Accordingly, if the strip packaging body 10 is bent along the bending section between rows 16, facing the medication 100 stored by the small medication storage cell 12 and the medication 100 stored by the large medication storage cell 14 is difficult when compared to the case where the lengths in the width direction for the first row 70 and the second row 72 are the same. Through these, even if the form of the medication 100 is of a tablet, the thickness of the strip packaging body 10 that is bent at the bending section between rows 16 can be reduced. If the thickness of the strip packaging body 10 is reduced, the space required for storage is reduced.

Figure 3:
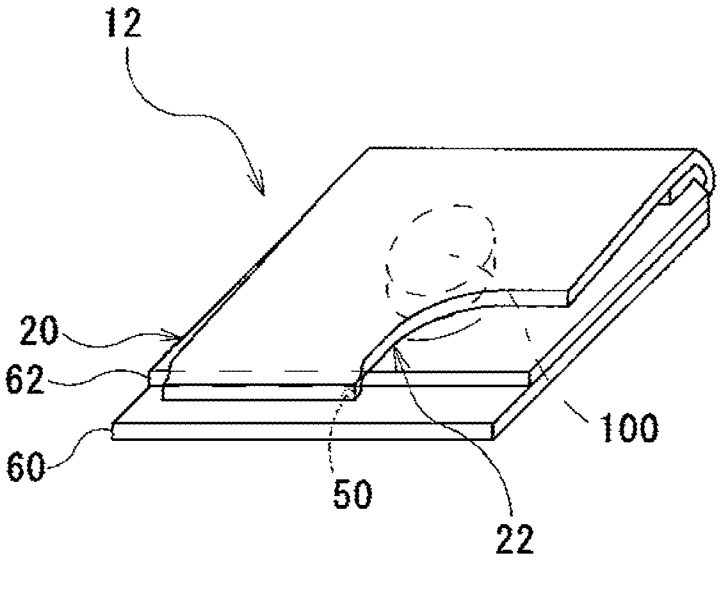
FIG. 3 Perspective view of the medication storage cell related to embodiment 1 of this invention.
Figure 4:
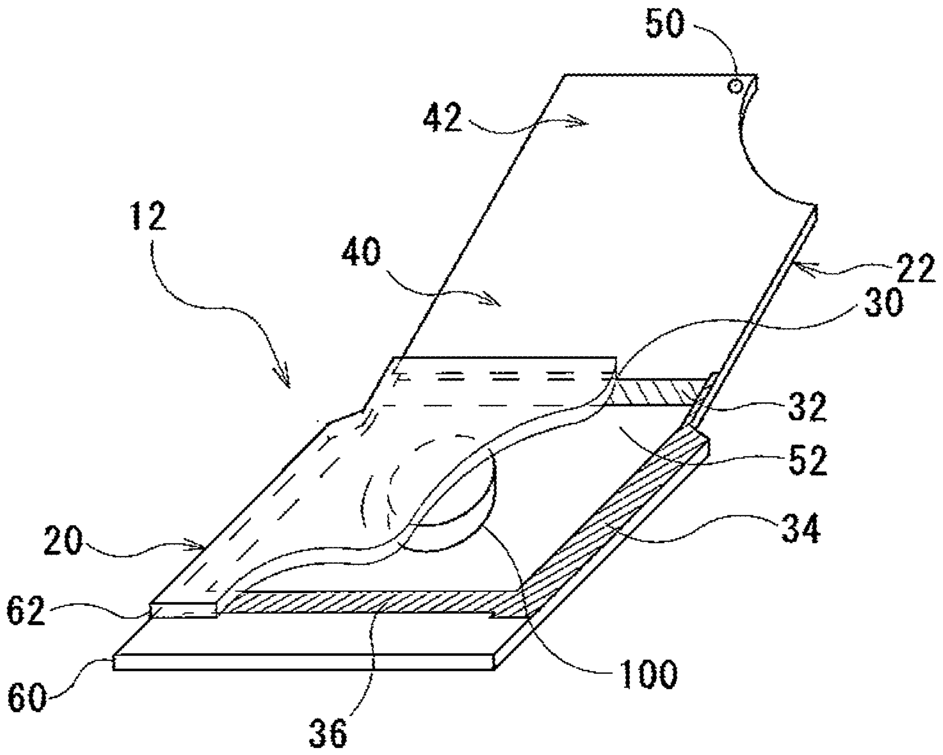
FIG. 4 Perspective view showing the tip end section of the interlocking piece in the separated state from the accommodating section of the medication storage cell related to embodiment 1 of this invention.

FIG. 3 is the perspective view of the small medication storage cell 12 related to this embodiment. FIG. 4 is the perspective view showing the tip end section 42 of the interlocking piece 22 in the separated state from the accommodating section 20 of the small medication storage cell 12 related to this embodiment. A part of the small medication storage cell 12 has been cut out in FIG. 4. The structure of the small medication storage cell 12 related to this embodiment is explained in reference to FIGS. 3 and 4. Moreover, as explained above, the structure of the small medication storage cell 12 and the structure of the large medication storage cell 14 is the same. Therefore, the description of the large medication storage cell 14 is omitted.

The small medication storage cell 12 related to this embodiment is obtained by bonding the interlocking piece attachment sheet 60 and cover sheet 62. The materials of these are well-known soft synthetic resins. The examples of synthetic resins are, polypropylene, polyvinyl alcohol, linear low density polyethylene and other low-density polyethylene, nylon, polyethylene terephthalate, and the material is formed by laminating at least two types of synthetic resin selected from the groups of these. The small medication storage cell 12 related to this embodiment is provided with an accommodating section 20 and an interlocking piece 22. The accommodating section 20 accommodates the medication 100. The interlocking piece 22 is provided on the interlocking piece attachment sheet 60. In this embodiment, the interlocking piece 22 is integrated with the interlocking piece attachment sheet 60.

As shown in FIG. 4, the outlet 30 for the medication 100 is provided at one end of the accommodating section 20. In this embodiment, the outlet 30 is formed by the interlocking piece attachment sheet 60 and the cover sheet 62 which are overlapped on each other. The cover sheet 62 is pasted to the interlocking piece attachment sheet 60 at an outlet region 32, an edge region 34, and a bottom region 36. The outlet region 32 is the region forming the outlet 30 described above. The edge region 34 is the region on both sides of the accommodating section 20. The bottom region 36 is the region at the bottom of the accommodating section 20. The inside of the accommodating section 20 is sealed by the pasting of the cover sheet 62 to the interlocking piece attachment sheet 60 at the outlet region 32, the edge region 34, and the bottom region 36. The adhesive strength between the interlocking piece attachment sheet 60 and the cover sheet 62 in the outlet region 32 is significantly lower than the adhesive strength between the interlocking piece attachment sheet 60 and the cover sheet 62 at the edge region 34 and the bottom region 36. In this embodiment, the interlocking piece attachment sheet 60 and the cover sheet 62 can be peeled off easily by rubbing the interlocking piece attachment sheet 60 and the cover sheet 62 in the outlet region 32 with fingers. Moreover, as apparent from FIG. 4, in this embodiment, the shape of the outlet region 32 is straight.

As shown in FIG. 4, the interlocking piece 22 has a base section 40 and a tip end section 42. The base section 40 is provided such that it is continuous with the outlet region 32 of the interlocking piece attachment sheet 60, and thus the edges of outlet 30. In this embodiment, the entire base section 40 is separated from the surface of the accommodating section 20. That is, the base section 40 is not bonded or stuck to the surface of the accommodating section 20. The tip end section 42 is provided such that it is continuous with the base section 40. With this, the interlocking piece 22 will move due to the bending and stretching with the interlocking piece attachment sheet 60 and the cover sheet 62. In this embodiment, the tip end section 42 is narrower than the base section 40. The tip end section 42 has a tip adhesive section 50.

As described above, the materials of the interlocking piece attachment sheet 60 and the cover sheet 62 are well-known soft synthetic resins. With this, the interlocking piece attachment sheet 60 and the cover sheet 62 can be bent. During distribution and storage, the small medication storage cell 12 is bent at the bending location 52. In this embodiment, the bending location 52 is positioned on the side where the medication 100 exists when viewed from the outlet region 32. The outlet 30 is closed by this bending and pasting on the outlet region 32. At this time, as shown in FIG. 3, the tip adhesive section 50 of the interlocking piece 22 is bonded to the surface of the accommodating section 20. In this embodiment, the other parts of the tip end section 42 except for the tip adhesive section 50 do not stick to the surface of the accommodating section 20.

Therefore, in this embodiment, the other parts of the interlocking piece 22 except for the tip adhesive section 50 are not stuck to the surface of the accommodating section 20.

[Explanation of Manufacturing Method]

The manufacturing method of the strip packaging body 10 related to this embodiment is explained below. As described above, the strip packaging body 10 related to this embodiment is provided with multiple numbers of the small medication storage cell 12 and multiple numbers of the large medication storage cell 14. Therefore, the manufacturing method of the strip packaging body 10 related to this embodiment is the manufacturing method of the small medication storage cell 12 and the large medication storage cell 14.

Figure 5:
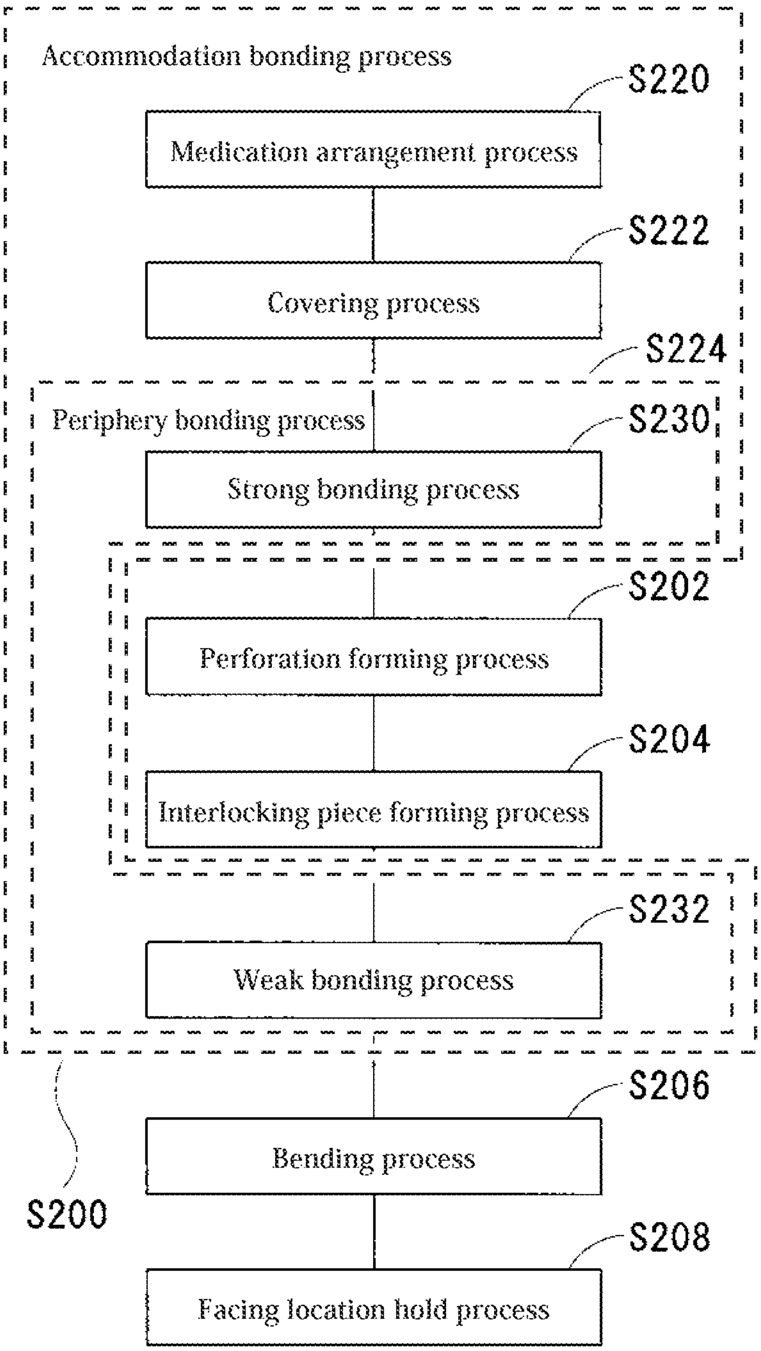
FIG. 5 Figure showing the process of the manufacturing method for the strip packaging body related to embodiment 1 of this invention.

FIG. 5 shows the process of the manufacturing method for the strip packaging body 10 related to this embodiment. As shown in FIG. 5, the manufacturing method for the strip packaging body 10 related to this embodiment comprises of an accommodation bonding process S200, a perforation forming process S202, an interlocking piece forming process S204, a bending process S206, and a facing location hold process S208. Below, the specific contents of these processes will be described.

In the accommodation bonding process S200, the medication 100 is accommodated between the interlocking piece forming sheet 110 and the cover forming body 112.

The interlocking piece forming sheet 110 is the material of the interlocking piece attachment sheet 60. The cover forming body 112 is the material of the cover sheet 62. Consequently, the interlocking piece forming sheet 110 and the cover forming body 112 are the material of the medication storage cell 12, 14. The material of the interlocking piece forming sheet 110 and the material of the cover forming body 112 are the soft synthetic resin described above. In the accommodation bonding process S200, the region around the periphery of the medication 100 between the interlocking piece forming sheet 110 and the cover forming body 112 is bonded such that the outlet 30 of the medication 100 is formed. The accommodation bonding process S200 related to this embodiment comprises of a medication arrangement process S220, a covering process S222, and a periphery bonding process S224.

In the medication arrangement process S220, the medication 100 is arranged on the surface of the interlocking piece forming sheet 110 placed on a base that is not shown. In this embodiment, robot 120 which is described below arranges the medication 100.

Figure 6:
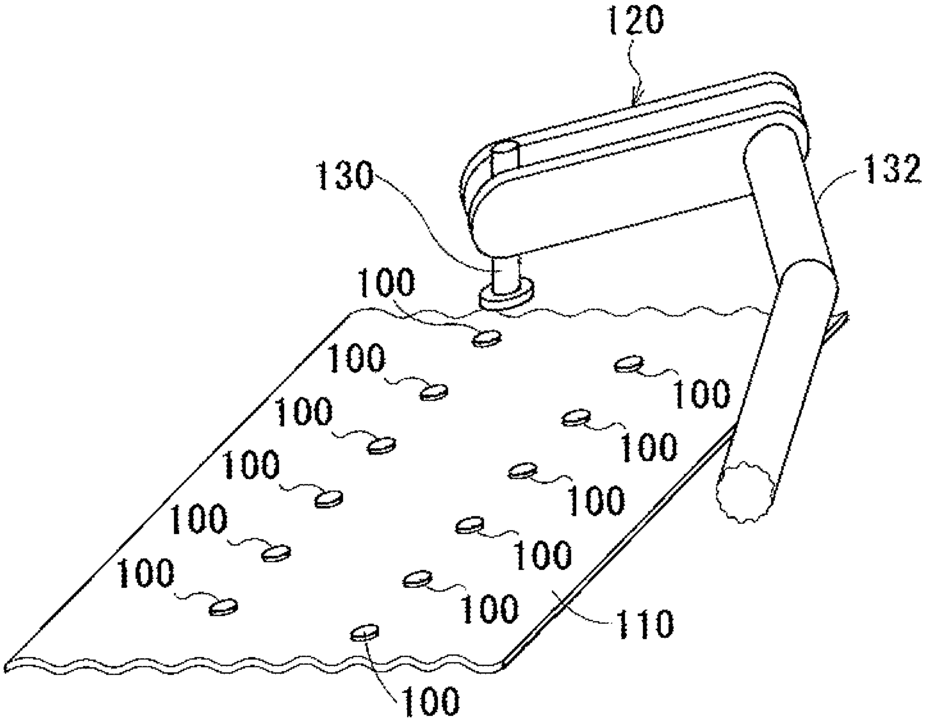
FIG. 6 Conceptual diagram showing the state of arrangement of the medication during the manufacturing of the strip packaging body related to embodiment 1 of this invention.

The robot 120 has a suction unit 130 for holding the medication 100, and a moving unit 132 to move the suction unit to any position on the surface of the interlocking piece forming sheet 110. Such the robot 120 is well known, and the description of which will not be repeated. FIG. 6 is a conceptual diagram illustrating the arrangement of the medication 100 by the robot 120 in the medication arrangement process S220. In this embodiment, two straight rows of the medication 100 are formed by the arrangement of the medication 100.

In the covering process S222, a device which is not shown other than the robot 120 described above, covers the medication 100 with two sheets of the cover forming body 112. That is, a part of the interlocking piece forming sheet 110 is covered by the cover forming body 112 for each the medication 100 arranged on the surface of the interlocking piece forming sheet 110. Since a device used for placing one object over another object is well known, the description of the device will not be repeated here. In this embodiment, two sheets of the cover forming body 112 cover respectively the medication 100 and a part of the interlocking piece forming sheet 110. In this embodiment, the part that is not covered by the cover forming body 112 among the end of the interlocking piece forming sheet 110 forms the interlocking part 160.

Figure 7:
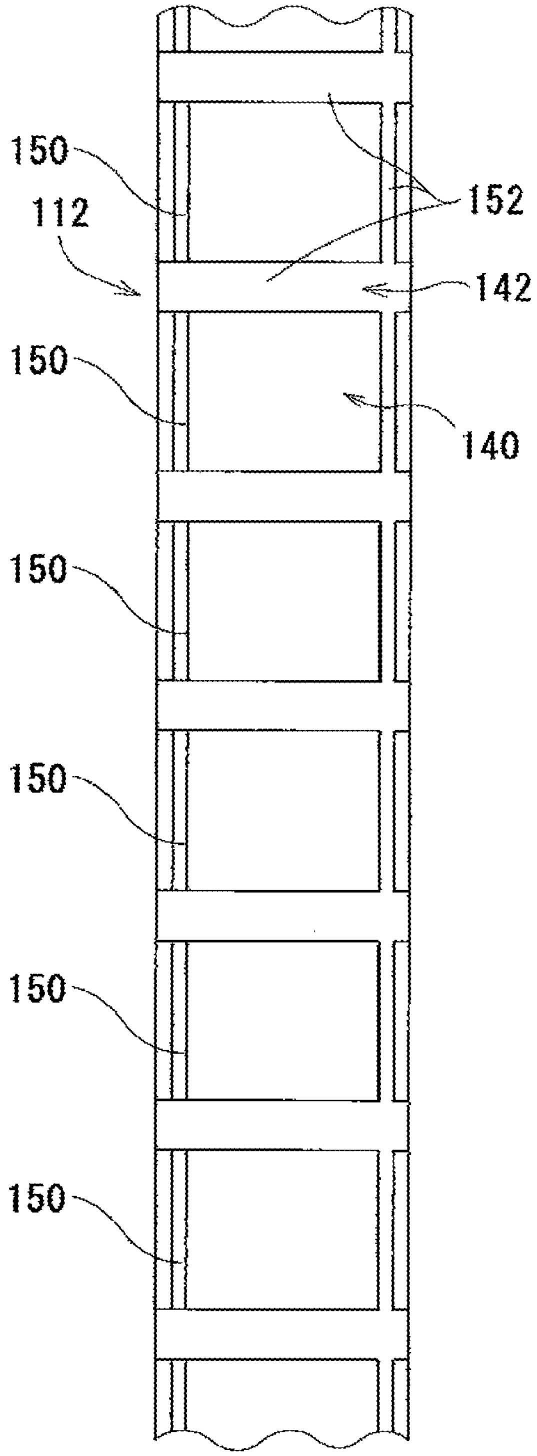
FIG. 7 Conceptual diagram showing the structure of the cover forming body related to embodiment 1 of this invention.

As described above, the cover forming body 112 is the material of the cover sheet 62. FIG. 7 is a conceptual diagram showing the structure of the cover forming body 112 related to this embodiment. In this embodiment, the cover forming body 112 is provided with an adhesive layer 142 on the sheet that is a base layer 140. The base layer 140 covers a part of the interlocking piece forming sheet 110 for each the medication 100. The material of the base layer 140 is a soft synthetic resin. Examples of synthetic resins are low density polyethylene, nylon, and polyethylene terephthalate. The adhesive layer 142 melts on heating. The adhesive layer 142 on melting and then solidifying again, bonds the base layer 140 and the interlocking piece forming sheet 110. In this embodiment, the adhesive layer 142 has a weak adhesive region 150 and a strong adhesive region 152. The adhesive strength of the weak adhesive region 150 is significantly lower than the adhesive strength of the strong adhesive region 152. The region of the base layer 140 and the interlocking piece forming sheet 110 which is bonded by the weak adhesive region 150 becomes the outlet region 32. The region of the base layer 140 and the interlocking piece forming sheet 110 which is bonded by the strong adhesive region 152 becomes the edge region 34 and the bottom region 36. By the cover forming body 112 covering a part of the interlocking piece forming sheet 110 for each the medication 100, the adhesive layer 142 faces the interlocking piece forming sheet 110.

In the periphery bonding process S224, the region around the periphery of the medication 100 between the interlocking piece forming sheet 110 and the cover forming body 112 is bonded. In this embodiment, specifically, the regions of the outlet region 32, the edge region 34, and the bottom region 36 are bonded. In this embodiment, the region which is bonded in this process are collectively called the "periphery region". The periphery bonding process S224 related to this embodiment comprises of a strong bonding process S230 and a weak bonding process S232.

In the strong bonding process S230, a region other than the predetermined region of the periphery region is bonded. The "predetermined region" described above is in the direction of the interlocking part 160 when viewed from the medication 100. As is clear from this fact, the predetermined region is a part of the periphery region. The predetermined region has the width through which the medication 100 can pass through.

The predetermined region is the region corresponding to the outlet region 32 described above. That is, the region heated by the strong bonding process S230 are the edge region 34 and the bottom region 36 of the periphery region described above. In the strong bonding process S230, a region other than the predetermined region of the periphery region is bonded by the device described below which is not shown. That device is provided with a heating unit and a pressing unit. The heating unit releases sufficient heat to melt the strong adhesive region 152 of the adhesive layer 142. The shape of the predetermined surface of the heating unit is the same as the edge region 34 and the bottom region 36 shown in FIG. 4. The pressing unit presses the predetermined surface of the heating unit to locations where the strong adhesive region 152 has been formed for the base layer 140 of the cover forming body 112. With this, the heat generated by the heating unit is transferred to the strong adhesive region 152 of the adhesive layer 142 through the base layer 140 of the cover forming body 112. When the heat is transferred to the strong adhesive region 152, the strong adhesive region 152 melts. After the strong adhesive region 152 has melted, the pressing unit separates the heating unit from the cover forming body 112. When the heating unit is separated from the cover forming body 112, the strong adhesive region 152 solidifies again. At that time, the strong adhesive region 152 bonds the base layer 140 and the interlocking piece forming sheet 110. With this, the locations of the edge region 34 and the bottom region 36 are bonded. Moreover, in this embodiment, the strong bonding process S230 is implemented in continuation of the covering process S222. The strong bonding process S230 is implemented at the locations where the covering process S222 has been implemented. With this, the risk of the interlocking piece forming sheet 110 and the cover forming body 112 shifting mutually before the interlocking piece forming sheet 110 and the cover forming body 112 solidifies mutually after the covering of the medication 100 can be reduced.

In the weak bonding process S232, the predetermined region described above of the periphery region is bonded. That is, the region in the outlet region 32 of the periphery region will be heated. In this embodiment, the predetermined region is heated by the same device that heated between the interlocking piece forming sheet 110 and the cover forming body 112 in the strong bonding process S230, which has not been shown. The pressing unit of the device presses the predetermined surfaces of the heating unit of the device to locations where the weak adhesive region 150 has been provided at the base layer 140 of the cover forming body 112. With this, the heat generated by the heating unit is transferred to the weak adhesive region 150 of the adhesive layer 142 through the base layer 140 of the cover forming body 112. When the heat is transferred to the weak adhesive region 150, the weak adhesive region 150 melts. After the weak adhesive region 150 has melted, the pressing unit separates the heating unit from the cover forming body 112. When the heating unit is separated from the cover forming body 112, the weak adhesive region 150 solidifies again. At that time, the weak adhesive region 150 bonds the base layer 140 and the interlocking piece forming sheet 110. With this, the region corresponding to the outlet region 32 is bonded. The region corresponding to the outlet region 32 is bonded such that the breaking strength is lower than the region bonded with the strong bonding process S230. That is, the predetermined region of the periphery region is bonded such that the breaking strength is lower than the region bonded with the strong bonding process S230. As a result, the periphery region is bonded such that the outlet 30 of the medication 100 is formed. The predetermined region becomes outlet 30 of the medication 100. In the periphery bonding process S224, the predetermined region is bonded such that the breaking strength is lower than the remaining part of the periphery region.

Figure 8:
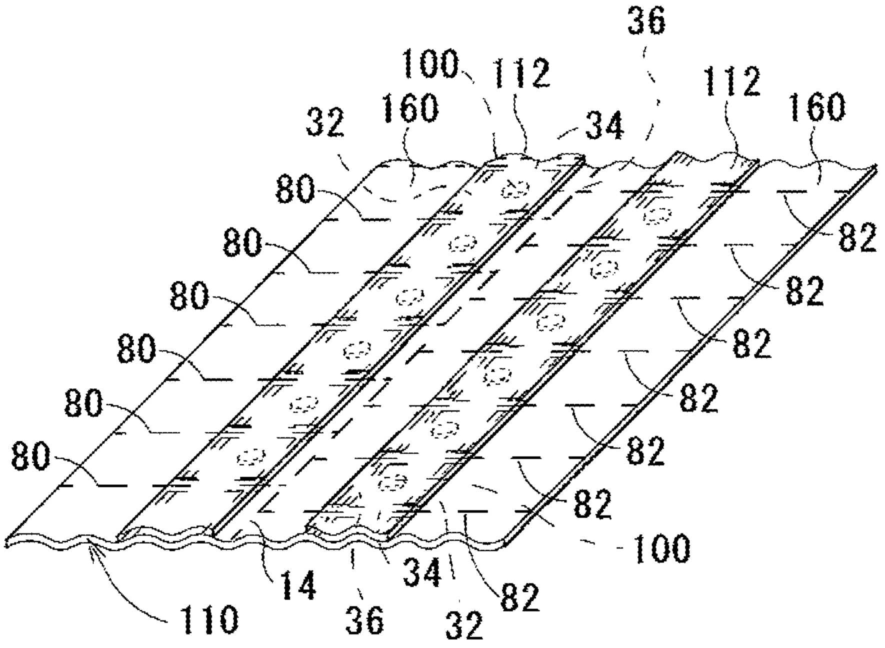
FIG. 8 Conceptual diagram showing the state where perforations are formed during the manufacturing of the strip packaging body related to embodiment 1 of this invention.

In the perforation forming process S202, a well-known perforation forming device which is not shown perforates the interlocking piece forming sheet 110 and the cover forming body 112. With this, perforations are formed at the locations of the boundary section 80 between two numbers of the small medication storage cell 12. Perforations are formed at the locations of the boundary section 82 between two numbers of the large medication storage cell 14. Perforations are also formed at the locations of the bending section between rows 16. FIG. 8 is the conceptual diagram showing the state where perforations have been formed in the perforation forming process S202.

Figure 9:
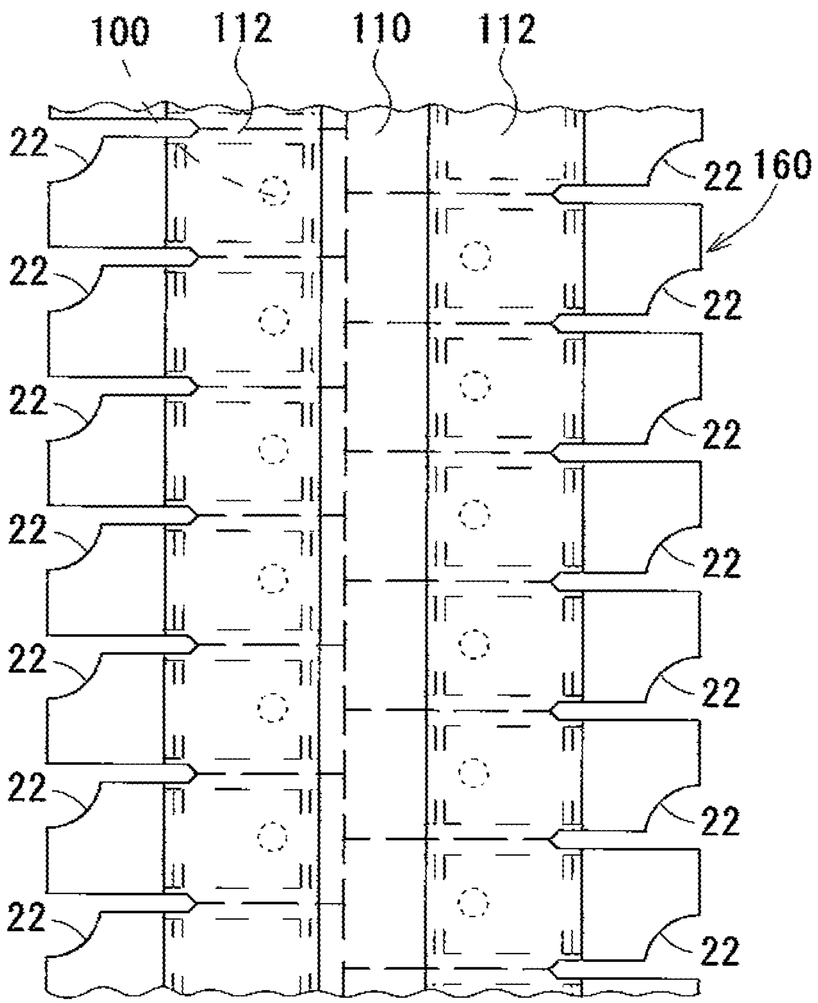
FIG. 9 Plan view of the interlocking piece forming sheet and the cover forming body during the manufacturing of the strip packaging body related to embodiment 1 of this invention.

In the interlocking piece forming process S204, a well-known cutting device which is not shown cuts out the locations described below. The locations are the location of boundary section 80 between two numbers of the small medication storage cell 12 and the location of boundary section 82 of two numbers of the large medication storage cell 14 in the interlocking piece forming sheet 110 and the cover forming body 112. At this time, the interlocking part 160 of the interlocking piece forming sheet 110 is cut out. With this, an outline of the interlocking piece 22 is formed. FIG. 9 is the plan view of the interlocking piece forming sheet 110 and the cover forming body 112 after the outline of the interlocking piece 22 has been formed in the interlocking piece forming process S204.

In the bending process S206, a well-known robot with the same structure as a human hand, folds the interlocking piece forming sheet 110 and the cover forming body 112. The locations which are bent corresponds to the bending location 52 described above. That is, the locations which are bent in this process are the predetermined locations in the direction where the interlocking part 160 is present when viewed from the medication 100 of the region where the cover forming body 112 overlaps to the interlocking piece forming sheet 110. With this, the part of the interlocking piece forming sheet 110 which is on the opposite side of the interlocking part 160 when viewed from the cover forming body 112 and the cover forming body 112 face the interlocking part 160. The location corresponding to the tip end section 42 of the interlocking piece 22 of the interlocking part 160 faces the region near the bending section between rows 16 of the interlocking piece forming sheet 110.

In the facing location hold process S208, the locations corresponding to the tip end section 42 of the interlocking piece 22 of the interlocking part 160 bonds with the locations described below. The locations are the locations that is faced by the locations corresponding to the tip end section 42 of the interlocking piece 22 of the interlocking part 160 with the bending process S206. The bonding is executed with the robot that is not shown and described below. The robot includes a heating element, an interlocking piece pressing unit, and a heating element pressing unit. The heating element generates enough heat to melt the locations corresponding to the tip end section 42 of the interlocking piece 22 of the interlocking part 160. The interlocking piece pressing unit presses the locations to the facing locations with the bending process S206. The heating element pressing unit presses the heating element to the locations corresponding to the tip end section 42 of the interlocking piece 22 of the interlocking part 160. With this, the part of the location corresponding to the tip end section 42 melts. The melted part bonds the locations corresponding to the tip end section 42 of the interlocking piece 22 and the interlocking piece forming sheet 110. After the bonding of these, the interlocking piece forming sheet 110 and the cover forming body 112 are cut to a predetermined length. With this, the strip packaging body 10 is completed.

[Explanation of the Usage Method]

The usage method of the strip packaging body 10 and the small medication storage cell 12 related to this embodiment is explained below. Moreover, the usage method of the large medication storage cell 14 is same as the usage method of the small medication storage cell 12. Therefore, the explanation of the usage method for the large medication storage cell 14 is omitted. During storage, the strip packaging body 10 is bent at the bending section between rows 16 and stored. During this period, the small medication storage cell 12 configuring the first row 70 is lined up such that it faces between two numbers of the large medication storage cell 14 configuring the second row 72. The large medication storage cell 14 configuring the second row 72 is lined up such that it faces between two numbers of the small medication storage cell 12 configuring the first row 70. The user when taking the medication 100, cuts out any one of the small medication storage cell 12 from the strip packaging body 10. The form of the small medication storage cell 12 which is cut out, is of the form shown in FIG. 3. After cutting the small medication storage cell 12, the user, inserts the thumb between the interlocking piece 22 and accommodating section 20. When the thumb is inserted, the tip adhesive section 50 is peeled off from the surface of the accommodating section 20. When the tip adhesive section 50 is peeled off, the small medication storage cell 12 changes from the state shown in FIG. 3 to the state shown in FIG. 4. Next, the user rubs the surface of the accommodating section 20 with the thumb and index finger. With this, the interlocking piece attachment sheet 60 and the cover sheet 62 receive mutually forces in the opposite direction. On receiving the force, the interlocking piece attachment sheet 60 and the cover sheet 62 are subjected to a shearing force. Then, as described above, the interlocking piece attachment sheet 60 and the cover sheet 62 can be peeled off easily at the outlet region 32. The outlet 30 opens when peeled off. When the outlet 30 is open, the user takes out the medication 100 and the medication 100 is dosed.

[Explanation of the Effect]

As described above, the small medication storage cell 12 and the large medication storage cell 14 related to this embodiment can be opened with the operation of inserting the thumb between the interlocking piece 22 and the accommodating section 20, and then rubbing the interlocking piece attachment sheet 60 and accommodating section cover sheet 62. The interlocking piece attachment sheet 60 and the cover sheet 62 are bent at the bending location 52 present on the side where the medication 100 exists when viewed from the outlet region 32 (front side than the outlet region 32 when viewed from near the center of the accommodating section 20). The adhesive strength of the outlet region 32 can be very less since the outlet 30 is closed by this bending. Since the adhesive strength can be very less, persons having little force at their fingertips, and those who can use only one hand will be able to easily open the small medication storage cell 12 and the large medication storage cell 14 related to this embodiment.

Also, in the small medication storage cell 12 and the large medication storage cell 14 related to this embodiment, the interlocking piece attachment sheet 60 and the cover sheet 62 are mutually pasted at the outlet region 32. Since they are pasted, the outlet 30 can be firmly closed while the tip end section 42 of the interlocking piece 22 is attached to the surface of the accommodating section 20, combined with the bending of the overlapping sheets (the interlocking piece attachment sheet 60 and the cover sheet 62) at the bending location 52. Furthermore, the shape of the outlet region 32 is straight. That is, the shape of the mutually pasted region of the overlapping sheets is straight. Since the shape of the outlet region 32 is a straight line, the possibility of centralization of the peeling force required to peel the outlet region 32 anywhere in that region is less compared to the case where any part of the outlet region 32 is curved. Since the possibility of centralization of the strength anywhere in the outlet region 32 is low in addition to closing of the outlet 30, therefore the adhesive strength of the outlet region 32 can be lowered when compared to the case where the possibility is not low. That is, since the possibility of centralization of the strength in the pasted region is low, in addition to the closing of the outlet due to the overlapping and bent sheets, and the mutually pasted region, the adhesive strength between the overlapping sheets can be lowered compared to the case otherwise. As a result, the outlet 30 can be easily opened even by persons who cannot move their fingertips dexterously, in addition that it can be sealed.

Also, in the strip packaging body 10 related to this embodiment, the large medication storage cell 14 configuring another row faces between two numbers of the small medication storage cell 12 configuring one row by bending at the bending section between rows 16. With this, the strip packaging body 10 bent at the bending section between rows 16 is not bulky compared to the case where the medication 100 is packed with a well-known packing film. If the strip packaging body 10 is not bulky, the space required for storage is reduced. The medication storage cell 12 configuring any one 70 of the multiple rows described above is arranged facing between any two adjacent the medication storage cell 14, 14 configuring another row 72 in the strip packaging body 10 related to this embodiment. When the former medication storage cell 12 faces between the latter two numbers of the medication storage cell 14, 14, when in a case described further, the medication 100 accommodated in the former medication storage cell 12 can be fitted between the medication 100 accommodated by the latter two numbers of medication storage cell 14, 14. That case is the case that the former medication storage cell 12 overlaps with any of the other row 72. The strip packaging body 10 will be not be bulky in the state where the former medication storage cell 12 overlaps with another row 72, when the medication 100 accommodated by the former medication storage cell 12 is fitted by the medication 100 which is accommodated by two numbers of the latter medication storage cell 14, 14, compared to the case where it is not. If the strip packaging body 10 is not bulky, the space required for storage is reduced.

Embodiment 2

Explanation of the Structure

Figure 10:
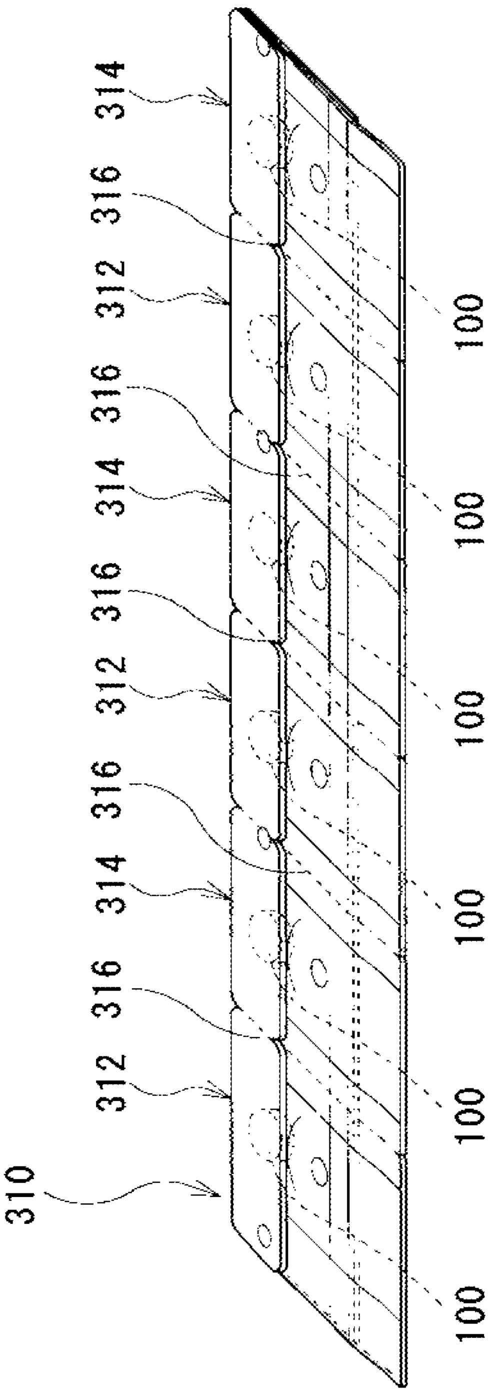
FIG. 10 Perspective view of the strip packaging body related to embodiment 2 of this invention.

FIG. 10 is the plan view of the strip packaging body 310 related to this embodiment. The strip packaging body 310 related to this embodiment is explained based on FIG. 10. The strip packaging body 310 related to this embodiment is provided with multiple numbers of first medication storage cell 312, and multiple numbers of second medication storage cell 314 and multiple numbers of connecting section 316.

The first medication storage cell 312 and second medication storage cell 314 accommodate the medication 100. As apparent from FIG. 10, the first medication storage cell 312 and the second medication storage cell 314 are alternately lined up to configure the row.

In this embodiment, the connecting section 316 is a straight line region arranged between the first medication storage cell 312 and the second medication storage cell 314. Perforations are provided in the connecting section 316. With this, it is possible to cut-off the first medication storage cell 312 and the second medication storage cell 314 easily.

Figure 11:
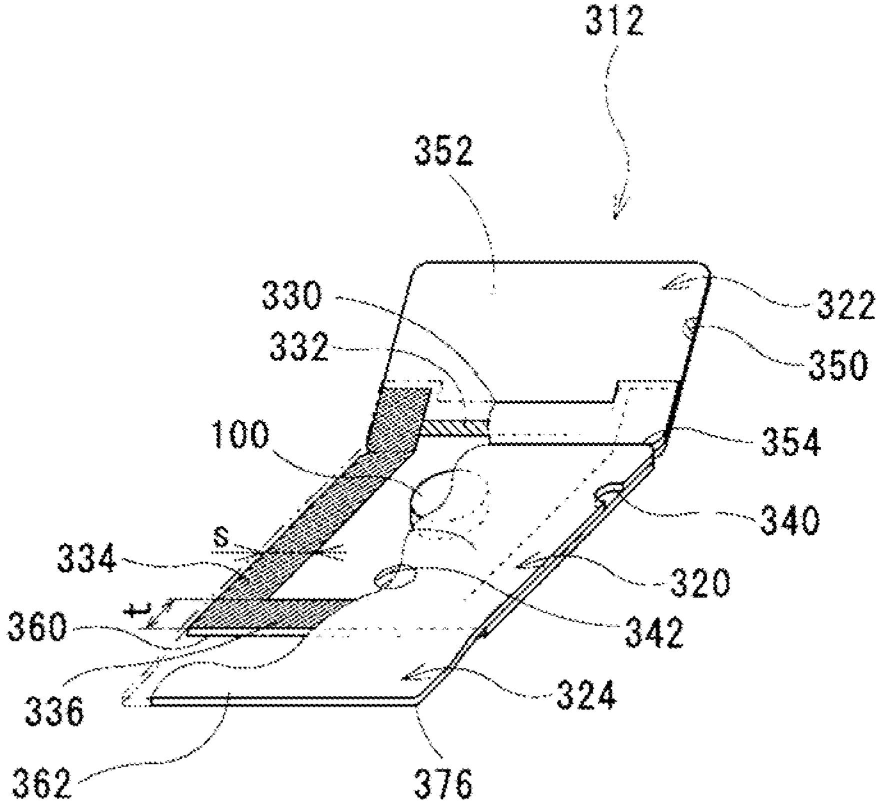
FIG. 11 Perspective view of the first medication storage cell related to embodiment 2 of this invention.

FIG. 11 is the perspective view of the first medication storage cell 312 related to this embodiment. A part of the first medication storage cell 312 has been cut out in FIG. 11. The structure of the first medication storage cell 312 related to this embodiment will be explained based on FIG. 11.

As shown in FIG. 11, the first medication storage cell 312 related to this embodiment is obtained by bonding the interlocking piece attachment sheet 360 and cover sheet 362. The first medication storage cell 312 related to this embodiment is provided with an accommodating section 320, interlocking piece 322, and label section 324. The accommodating section 320 accommodates the medication 100. The interlocking piece 322 protrudes from one end of the accommodating section 320. The label section 324 protrudes from the other end of the accommodating section 320.

As shown in FIG. 11, the cover sheet 362 is bonded to the interlocking piece attachment sheet 360 at the edge region 334, and bottom region 336. With this, the accommodating section 320 is formed. The edge region 334 is the region on both sides of the accommodating section 320. The bottom region 336 is the region at the bottom of the accommodating section 320. In this embodiment, the width s (length of the edge region 334 in the perpendicular direction of the adhesive region 332 when viewed from the medication 100 in FIG. 11) of the edge region 334, and width t (length of the bottom region 336 in the direction of the adhesive region 332 when viewed from the medication 100 in FIG. 11) of the bottom region 336 are both 3.0 mm. Incidentally, it is preferable that the width of the edge region 334 and width of the bottom region 336 is narrow. However, it is preferable that the width of the edge region 334 and the width of the bottom region 336 is more than 2.0 mm up to 3.0 mm. This is because the width can be accurately formed with a general-purpose machine. The medication 100 is sandwiched between the interlocking piece attachment sheet 360 and the cover sheet 362 by the bonding of the cover sheet 362 to the interlocking piece attachment sheet 360 at the edge region 334, and the bottom region 336.

In this embodiment, the accommodating section 320 has a limiting section 342. The limiting section 342 restricts the movable range of the medication 100 within the accommodating section 320. In this embodiment, the limiting section 342 is achieved by the interlocking piece attachment sheet 360 and the cover sheet 362 bonding together.

In this embodiment, information is displayed on the label section 324. An example of the information is the type of the medication 100. The outer edge section 376 having a curved contour is provided at the corners of the label section 324. The outer edge section 376 provided in the corners of the label section 324 is less likely to cause damage to the internal organs when a person swallows the first medication storage cell 312 by mistake, when compared to right angle or acute angle corners. Furthermore, it is preferable that an outer edge section having a curved contour is provided at the corners of the interlocking piece 322, or the corners of the bent location 354 of the accommodating section 320 in the state in which the interlocking piece 322 is bonded through the cut out with the outer edge adhesive section 350 (outer edge adhesive section 350 will be described below), namely, bent such that the outlet 330 is closed.

As shown in FIG. 11, the outlet 330 for the medication 100 is provided at one end of the accommodating section 320. The cover sheet 362 is bonded to the interlocking piece attachment sheet 360 at the adhesive region 332 in addition to the edge region 334 and the bottom region 336. In this embodiment, the region from the adhesive region 332 to the bending location 354 of the interlocking piece attachment sheet 360 is the outlet sheet section of the interlocking piece attachment sheet 360. The region from the adhesive region 332 to the bent location 354 of the cover sheet 362 is the outlet sheet section of the cover sheet 362. The inside of the accommodating section 320 is sealed by the adhesion of the cover sheet 362 to the interlocking piece attachment sheet 360 at the adhesive region 332, and the edge region 334, and the bottom region 336.

The adhesive strength between the interlocking piece attachment sheet 360 and the cover sheet 362 in the adhesive region 332 is significantly lower compared to the adhesive strength between the interlocking piece attachment sheet 360 and the cover sheet 362 in the edge region 334 and the bottom region 336. In this embodiment, the interlocking piece attachment sheet 360 and the cover sheet 362 can be peeled off easily by rubbing the interlocking piece attachment sheet 360 and the cover sheet 362 in the adhesive region 332 with the palm. Moreover, in this embodiment as is clear from the FIG. 11, the shape of the adhesive region 332 is straight.

In this embodiment, the interlocking piece 322 is formed from a part of the interlocking piece attachment sheet 360. With this, the interlocking piece 322 will move due to the bending and stretching with the interlocking piece attachment sheet 360 and the cover sheet 362. In this embodiment, the interlocking piece 322 has an outer edge adhesive section 350 and a knob 352.

During distribution and storage, the first medication storage cell 312 is bent. The bent locations correspond to bending location 354 shown in FIG. 11. In this embodiment, the bending location 354 is positioned at the side where the medication 100 eventually the bottom region 336, when viewed from the adhesive region 332. The outlet 330 is closed by this bending and pasting of the adhesive region 332. At this time, the outer edge adhesive section 350 of the interlocking piece 322 is bonded to the part of the interlocking piece attachment sheet 360 configuring the accommodating section 320, through the cut out section 340 of the cover sheet 362. The sealant layers described later face each other by the provision of the cut-out and can be securely bonded. With this, the interlocking piece 322 restrains a part of the interlocking piece attachment sheet 360 and the cover sheet 362 to maintain the bent state of those sheets which have been to close the outlet.

In this embodiment, the knob section 352 is located at the tip part of the interlocking piece 322. The knob section 352 can be held by the fingers of a person when the outer bonding section 350 is peeled off.

Figure 12:
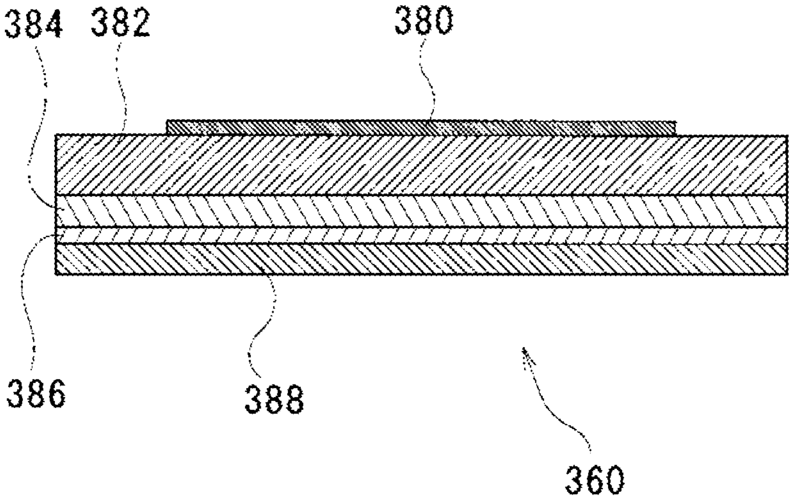
FIG. 12 Cross-sectional view of the interlocking piece attachment sheet related to embodiment 2 of this invention.

FIG. 12 is the cross-sectional view of the interlocking piece attachment sheet 360 related to this embodiment. The structure of the interlocking piece attachment sheet 360 related to this embodiment will be explained in detail based on FIG. 12. The interlocking piece attachment sheet 360 related to this embodiment has a primary barrier layer 380, a sealant layer 382, an adhesive layer 384, a secondary barrier layer 386 and a surface layer 388. The primary barrier layer 380 is the layer which absorbs the oxygen from the inside of the accommodating section 320. The primary barrier layer 380 is also the layer preventing the entry of oxygen and water vapor from the outside to the inside of the accommodating section 320. In this embodiment, the material of the primary barrier layer 380 is fluoropolymer. In this embodiment, the primary barrier layer 380 is located on the inner side of the accommodating section 320. The primary barrier layer 380 is in contact with the medication 100. That is, the primary barrier layer 380 is the inner layer of the accommodating sheet section. The sealant layer 382 is the layer maintaining an airtight state inside of the accommodating section 320. The sealant layer 382 is the layer which is melted when the interlocking piece attachment sheet 360 and the cover sheet 362 are bonded together. In this embodiment, the material of the sealant layer 382 is polyethylene. The adhesive layer 384 is the layer bonding the sealant layer 382 and the secondary barrier layer 386. In this embodiment, the material of the adhesive layer 384 is also polyethylene. The secondary barrier layer 386 is the layer preventing the entry of oxygen and water vapor from the outside to the inside of the accommodating section 320. In this embodiment, the material of the secondary barrier layer 386 is alumina. The surface layer 388 is the layer protecting the secondary barrier layer 386. In this embodiment, the material of the surface layer 388 is polyethylene terephthalate. In this embodiment, the surface layer 388 is located on the outer side of the accommodating section 320. That is, the surface layer 388 is the outer layer of the accommodating sheet section.

In this embodiment, the material of the interlocking piece attachment sheet 360 meets the following requirements. The first requirement is the requirement that the water vapor permeability must be less than 1.0 $g/m^2/day$. Water vapor permeability of less than 0.5 $g/m^2/day$ is more preferable. The second requirement is the requirement that the oxygen permeability must be less than 600 nano $m^3/m^2/day/atm$ (0.6 $cc/m^2/day/atm$). Oxygen permeability of less than 300 nano $m^3/m^2/day/atm$ (0.3 $cc/m^2/day/atm$) is more preferable. The third requirement is the requirement that the static friction coefficient of the surfaces on the inner side of the accommodating section 320 must be less than the static friction coefficient of the surface exposed to the outer side of the accommodating section 320. Static friction coefficient of 0.5 is preferable for the surfaces on the inner side of the accommodating section 320. A value of 0.2 or less is more preferable. The fourth requirement is the requirement that the young's modulus must be more than 200 Mpa and below 1000 Mpa. Young's modulus more than 400 Mpa and below 600 Mpa is more preferable. The possibility of the accommodating section 320 damaging the internal organs when a person swallows the first medication storage cell 312 or the second medication storage cell 314 by mistake is reduced compared to the case where the Young's modulus exceeds 1000 MPa since the material of the interlocking piece attachment sheet 360 satisfies the fourth requirement. The fifth requirement is the requirement that when the interlocking piece attachment sheet 360 and the cover sheet 362 are bonded together, the water vapor and oxygen permeability of the bonded locations must be the same or less than that of the interlocking piece attachment sheet 360 material. The sixth requirement is the requirement that the interlocking piece attachment sheet 360 and the cover sheet 362 which are bonded together can be easily peeled off by the hands of a person.

In this embodiment, the material of the cover sheet 362 is the same as the material of the interlocking piece attachment sheet 360. Therefore, the explanation of the cover sheet 362 material of this embodiment will be omitted.

Moreover, the structure of the second medication storage cell 314 is the same as the structure of the first medication storage cell 312 except for the two points described below. The first point is the point that the position of the cut out section 340 is on the opposite side of the first medication storage cell 312 when viewed from the position where the medication 100 is positioned. The second point is the point that the position of the outer edge adhesive section 350 is also on the opposite side of the first medication storage cell 312 when viewed from the position where the medication 100 is positioned. Therefore, the description of the second medication storage cell 314 is omitted.

[Explanation of the Manufacturing System]

Figure 13:
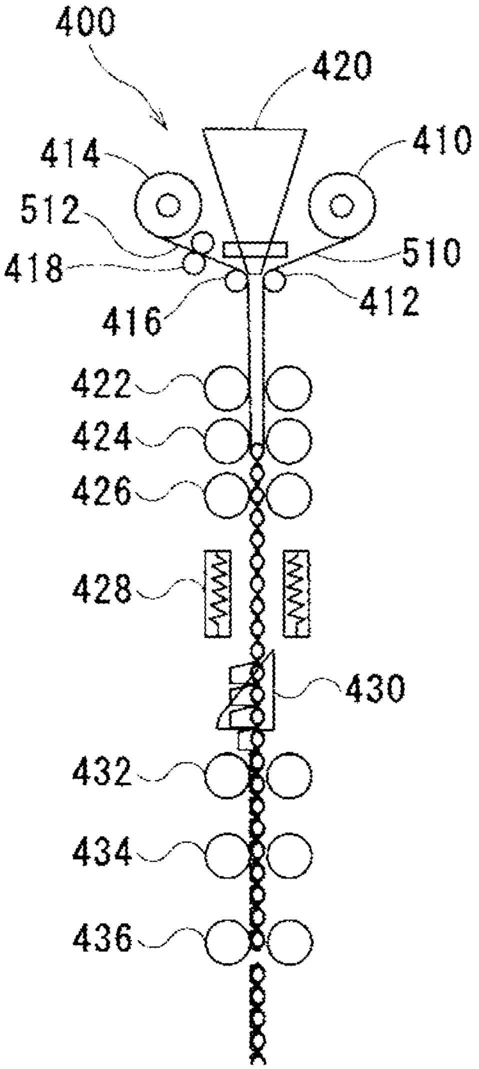
FIG. 13 Conceptual diagram showing the structure of the strip packaging body manufacturing system related to embodiment 2 of this invention.

FIG. 13 is the conceptual diagram showing the structure of a strip packaging body manufacturing system 400 related to this embodiment. The structure of the strip packaging body manufacturing system 400 related to this embodiment is explained based on FIG. 13.

The strip packaging body manufacturing system 400 related to this embodiment is equipped with a first material sheet drawing device 410, a first guide roller 412, a second material sheet drawing device 414, a second guide roller 416, a cut out forming roller unit 418, a tablet supply unit 420, a vertical bonding roller unit 422, a horizontal bonding roller unit 424, a perforations forming roller unit 426, a heating device 428, a bending guide unit 430, a press roller unit 432, a facing location bonding roller unit 434 and a cutting roller unit 436.

The first material sheet drawing device 410 is the device which pulls out one end of the interlocking piece forming sheet 510 which is wound into a cylindrical shape. The drawn interlocking piece forming sheet 510 enters at the bottom of the tablet supply unit 420 through the first guide roller 412. The interlocking piece forming sheet 510 which enters at the bottom of the tablet supply unit 420 hangs by its own weight. The second material sheet drawing device 414 is the device which pulls out one end of the cover forming body 512 which is wound into a cylindrical shape. The drawn cover forming body 512 enters at the bottom of the tablet supply unit 420 through the second guide roller 416. The cover forming body 512 which enters at the bottom of the tablet supply unit 420 also hangs by its own weight. With the entry to bottom of the tablet supply unit 420, the cover forming body 512 faces the interlocking piece forming sheet 510.

The cut out forming roller unit 418 forms a cut out in the cover forming body 512. The cut out forming roller unit 418 has a receiving roller and a pressing roller. The receiving roller supports the cover forming body 512. The pressing roller presses the cover forming body 512 to the receiving roller. At that time, the pressing roller forms a cut out in the region corresponding to the cut out section 340 of the cover sheet 362 out of the cover forming body 512. The pressing roller has a protrusion which is not shown. It becomes possible to form the cut out with this protrusion by pressing to the region corresponding to the cut out section 340.

The tablet supply unit 420 drops the tablets between the interlocking piece forming sheet 510 drawn by the first material sheet drawing device 410, and the cover forming body 512 drawn by the second material sheet drawing device 414. In this embodiment, the tablet is the medication 100 of this embodiment. The interlocking piece forming sheet 510 and the cover forming body 512 into which the tablet has been dropped are further drawn by the first material sheet drawing device 410 and second material sheet drawing device 414 and enter the vertical bonding roller unit 422.

The vertical bonding roller unit 422 bonds the interlocking piece forming sheet 510 and the cover forming body 512. The vertical bonding roller unit 422 has the receiving roller, first pressing roller, second pressing roller, first heater, second heater, and cooling unit. The receiving rollers support the interlocking piece forming sheet 510 and the cover forming body 512. The first pressing roller presses the interlocking piece forming sheet 510 and the cover forming body 512 to the receiving roller. At this time, the first pressing roller transfers heat to the interlocking piece forming sheet 510 and the cover forming body 512. The interlocking piece forming sheet 510 and the cover forming body 512 to which heat is transferred melt. They are bonded together due to the melting. The first pressing roller has a protrusion which is not shown. The protrusion by pressing the region corresponding to the bottom region 336 is able to transfer the heat to that region. The first heater supplies heat to the first pressing roller. The second pressing roller presses the interlocking piece forming sheet 510 and the cover forming body 512 to the receiving roller at the same time with the pressure applied by the first pressing roller. At this time, the second pressing roller transfers heat to the interlocking piece forming sheet 510 and the cover forming body 512 in the same way as the first pressing roller. The second pressing roller has a protrusion similar to the first pressing roller which is not shown. The protrusion by pressing the region corresponding to the adhesive region 332 is able to transfer the heat to that region. The second heater supplies heat to the second pressing roller. The cooling unit cools the first pressing roller and the second pressing roller immediately after the completion of the bonding between the interlocking piece forming sheet 510 and the cover forming body 512. The interlocking piece forming sheet 510 bonded with the cover forming body 512 by the vertical bonding roller unit 422 is further drawn by the first material sheet drawing device 410 and the second material sheet drawing device 414, and enters the perforations forming roller unit 426.

The horizontal adhesive roller unit 424 also bonds the interlocking piece forming sheet 510 and the cover forming body 512. The horizontal bonding roller unit 424 has the receiving roller, pressing roller, heater, and the cooling unit. The receiving roller supports the interlocking piece forming sheet 510 and the cover forming body 512. The pressing roller presses the interlocking piece forming sheet 510 and the cover forming body 512 to the receiving roller. At this time, the pressing roller transfers heat to the interlocking piece forming sheet 510 and the cover forming body 512. The interlocking piece forming sheet 510 and the cover forming body 512 to which heat is transferred melt. They are bonded together due to the melting. The pressing roller has a protrusion which is not shown. The protrusion by pressing the region corresponding to the edge region 334 is able to transfer the heat to that region. The heater supplies heat to the pressing roller. The cooling unit cools the pressing roller immediately after the completion of the bonding between interlocking piece forming sheet 510 and the cover forming body 512. The interlocking piece forming sheet 510 bonded with the region corresponding to the edge region 334 by the horizontal bonding roller unit 424 is further drawn by the first material sheet drawing device 410 and the second material sheet drawing device 414, and enters the perforations forming roller unit 426.

The perforations forming roller unit 426 forms the perforations at the region corresponding to the connecting section 316 of the interlocking piece forming sheet 510 and the cover forming body 512 bonded region. The perforations forming roller unit 426 forms a cut out at the edge of the perforations. The perforations forming roller unit 426 has a receiving roller and a pressing roller. The receiving roller supports the interlocking piece forming sheet 510 and the cover forming body 512. The pressing roller presses the interlocking piece forming sheet 510 and the cover forming body 512 to the receiving roller. At this time, the pressing roller forms the perforations in the interlocking piece forming sheet 510 and the cover forming body 512. The pressing roller has a protrusion which is not shown. The protrusion by pressing the region corresponding to the connecting section 316 is able to form the perforations and cut out at the edge in that region. The interlocking piece forming sheet 510 and the cover forming body 512 in which the perforations has been formed are further drawn by the first material sheet drawing device 410 and the second material sheet drawing device 414, and enter the heating device 428.

The heating device 428 heats the region corresponding to the outlet sheet region of the first medication storage cell 312 and the second medication storage cell 314 of the interlocking piece forming sheet 510 and the cover forming body 512. In this embodiment, the heating device 428 has a pair of infrared heaters. These infrared heaters are pressed on the outlet sheet region of the first medication storage cell 312 and the second medication storage cell 314. With this, the region corresponding to the outlet sheet region is heated. The region corresponding to the outlet sheet region becomes soft due to the heat. The region corresponding to the outlet sheet region can be bent easily since it has become soft. The region corresponding to the outlet sheet section with the interlocking piece forming sheet 510 and the cover forming body 512 are further drawn by the first material sheet drawing device 410 and the second material sheet drawing device 414, and passes through the bending guide unit 430.

The bending guide unit 430 guides the interlocking piece forming sheet 510 and the cover forming body 512 such that the interlocking piece forming sheet 510 and the cover forming body 512 bend at the locations corresponding to the bending location 354 of the medication storage cell 12. To provide such guidance, the bending guide unit 430 has surfaces that come in contact with the interlocking piece forming sheet 510 and the cover forming body 512, when they pass through the bending guide unit 430. The interlocking piece forming sheet 510 and the cover forming body 512 pass through the bending guide unit 430 while in contact with the surfaces, and by this the interlocking piece forming sheet 510 and the cover forming body 512 bend at the locations corresponding to the bending location 354 of the medication storage cell 12. The interlocking piece forming sheet 510 and the cover forming body 512 that is bent at these locations are further drawn by the first material sheet drawing device 410 and the second material sheet drawing device 414, and enter the press roller unit 432.

The press roller unit 432 forms folds at the locations corresponding to the bending location 354 of the first medication storage cell 312 and the second medication storage cell 314. The interlocking piece forming sheet 510 and the cover forming body 512 in which the folds have been formed, enters the facing location bonding roller unit 434.

The facing location bonding roller unit 434 bonds the parts of the interlocking piece forming sheet 510 forming the accommodating section 320, with the locations corresponding to the outer edge adhesive section 350 of the interlocking piece forming sheet 510 through the location corresponding to the cut out 340 of the cover sheet 362 of the cover forming body 512. The interlocking piece forming sheet 510 and the cover forming body 512 which have been bonded are further drawn by the first material sheet drawing device 410 and the second material sheet drawing device 414 and enter the cutting roller unit 436.

The cutting roller unit 436 cuts the interlocking piece forming sheet 510 and the cover forming body 512 to a predetermined length. The configuration of the cutting roller unit 436 is similar to the perforations forming roller unit 426. Accordingly, the explanation of the cutting roller unit 436 configuration will not be repeated. The interlocking piece forming sheet 510 and the cover forming body 512 which is cut by the cutting roller unit 436 will form the strip packaging body 310 of this embodiment.

[Explanation of the Manufacturing Method]

Figure 14:
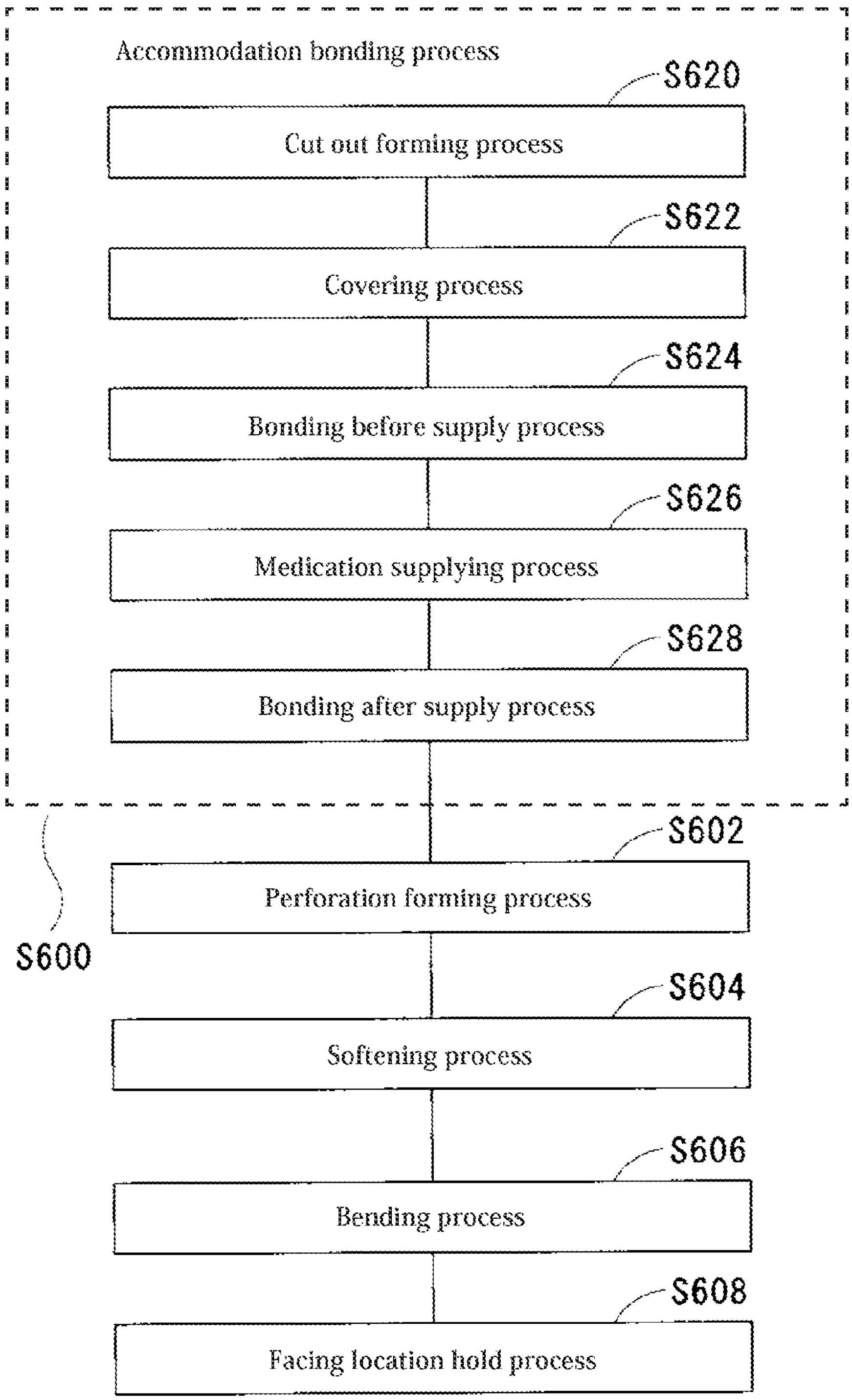
FIG. 14 Figure showing the process of the manufacturing method for the strip packaging body related to embodiment 2 of this invention.

FIG. 14 shows the process of the manufacturing method for the strip packaging body 310 related to this embodiment. In this embodiment, the strip packaging body 310 is manufactured by the strip packaging body manufacturing system 400 described above.

The manufacturing method of the strip packaging body 310 related to this embodiment is explained below based on FIGS. 13 and 14. As described above, the strip packaging body 310 related to this embodiment is provided with multiple numbers of the first medication storage cell 312, and multiple numbers of the second medication storage cell 314. Therefore, the manufacturing method of the strip packaging body 310 related to this embodiment is the manufacturing method of the first medication storage cell 312 and the second medication storage cell 314.

The manufacturing method for the strip packaging body 310 related to this embodiment comprises of an accommodation bonding process S600, a perforation forming process S602, a softening process S604, a bending process S606, and a facing location hold process S608. Each process of the manufacturing method of the strip packaging body 310 related to this embodiment is explained in detail below.

In the accommodation bonding process S600, the medication 100 is accommodated between the interlocking piece forming sheet 510 and the cover forming body 512. The interlocking piece forming sheet 510 is the material of the interlocking piece attachment sheet 360. The cover forming body 512 is the material of the cover sheet 362. Consequently, the interlocking piece forming sheet 510 and the cover forming body 512 are the material of the first medication storage cell 312 and second medication storage cell 314. In the accommodation bonding process S600, the region around the periphery of the medication 100 of the region between the interlocking piece forming sheet 510 and the cover forming body 512 is bonded. With this, the outlet 330 is formed. The accommodation bonding process S600 related to this embodiment comprises of a cut out forming process 5620, a covering process S622, a bonding before supply process S624, a medication supplying process S626, and a bonding after supply process S628.

In the cut out forming process 5620, the second material sheet drawing device 414 pulls out one end of the cover forming body 512 which is wound into a cylindrical shape. The cut out forming roller unit 418 forms a cut out in the cover forming body 512 which is drawn by the second material sheet drawing device 414. The cover forming body 512 with the cut out enters at the bottom of the tablet supply unit 420 through the second guide roller 416.

In the covering process S622, the first material sheet drawing device 410 pulls out one end of the interlocking piece forming sheet 510. The drawn interlocking piece forming sheet 510 enters at the bottom of the tablet supply unit 420 through the first guide roller 412. The interlocking piece forming sheet 510 which enters at the bottom of the tablet supply unit 420 faces the cover forming body 512 which enters at the bottom of the tablet supply unit 420 at a slightly shifted state. As a result, in this embodiment, the cover forming body 512 covers a part of the interlocking piece forming sheet 510. The interlocking piece forming sheet 510 covers a part of the cover forming body 512. In this embodiment, the part that is not covered by the cover forming body 512 among the edge of the interlocking piece forming sheet 510 is called the "material edge".

In the bonding before supply process S624, the vertical bonding roller unit 422 bonds the region corresponding to the bottom region 336 and the region corresponding to the adhesive region 332 of the region between the interlocking piece forming sheet 510 and the cover forming body 512. With this, the heat transferred by the first pressing roller and the second pressing roller of the vertical bonding roller unit 422, is transferred to the sealant layer 382 through the surface layer 388 of the cover forming body 512. When heat is transferred to the sealant layer 382, the sealant layer 382 melts. Once the sealant layer 382 melts, the first pressing roller and the second pressing roller are separated from the cover forming body 512. Once the first pressing roller and the second pressing roller are separated from the cover forming body 512, the sealant layer 382 solidifies again. At that time, the sealant layer 382 bonds the cover forming body 512 and the interlocking piece forming sheet 510. With this, the regions corresponding to the bottom region 336 and the regions corresponding to the adhesive region 332 are bonded. In this embodiment, the temperature of the first pressing roller and the second pressing roller of the vertical bonding roller unit 422 is different. With this, the adhesive strength of the regions corresponding to the bottom region 336 and the adhesive strength of the regions corresponding to the adhesive region 332 differ.

In the medication supplying process S626, the tablet supply unit 420 drops the tablets between the interlocking piece forming sheet 510 and the cover forming body 512. With this, the tablet fits between the regions corresponding to the bottom region 336 and the regions corresponding to the adhesive region 332.

In the bonding after supply process S628, the region around the periphery of the medication 100 of the region between the interlocking piece forming sheet 510 and the cover forming body 512 is bonded by the horizontal bonding roller unit 424. In this embodiment, specifically, the region corresponding to the edge region 334 described above is bonded. The pressing roller of the horizontal bonding roller unit 424 transfers heat to the interlocking piece forming sheet 510 and the cover forming body 512. The heat transferred by the pressing rollers is transferred to the sealant layer 382 through the surface layer 388 of the cover forming body 512. When heat is transferred to the sealant layer 382, the sealant layer 382 melts. Once the sealant layer 382 melts, the pressing rollers are separated from the cover forming body 512. Once the pressing rollers are separated from the cover forming body 512, the sealant layer 382 solidifies again. At that time, the sealant layer 382 bonds the cover forming body 512 and the interlocking piece forming sheet 510. With this, the region corresponding to the edge region 334 is bonded.

In the perforation forming process S602, the perforations forming roller unit 426 forms the perforations and cut outs in the interlocking piece forming sheet 510 and the cover forming body 512. With this, the perforations are provided at the locations of the connecting section 316 between first the medication storage cell 312 and the second medication storage cell 314. The cut out is formed at the edge of the perforations. Any of the cut out forms the outer edge section 376 of the corners of the label section 324.

In the softening process S604, the heating device 428 heats the region corresponding to the outlet sheet region of the interlocking piece attachment sheet 360 and the cover sheet 362. With this, the heat transferred by the heating device 428 is transferred to the region. When heat is transferred to this region, the region becomes soft.

In the bending process S606, the bending guide unit 430 guides the interlocking piece forming sheet 360 and the cover sheet 362 such that the interlocking piece forming sheet 360 and the cover sheet 362 bend at the locations corresponding to the bending location 354. The press roller unit 432 forms folds at the locations corresponding to the bending location 354.

In the facing location hold process S608, the facing location bonding roller unit 434 bonds the parts configuring the accommodating section 320 of the interlocking piece forming sheet 510 with the locations corresponding to the outer edge adhesive section 350 of the interlocking piece forming sheet 510. These locations are bonded through the locations corresponding to the cut out section 340 of the cover sheet 362 out of the cover forming body 512. After the bonding of these locations, the cutting roller unit 436 cuts the interlocking piece forming sheet 510 and the cover forming body 512 to a predetermined length. With this, the strip packaging body 310 is completed.

[Explanation of the Usage Method]

The usage method of the strip packaging body 310, and first medication storage cell 312 and second medication storage cell 314 related to this embodiment are explained below. During storage, the strip packaging body 310 is bent at any one of the connecting section 316 and stored. The user when using the medication 100, cuts out any one of the first medication storage cell 312 and the second medication storage cell 314 from the strip packaging body 310. The user after cutting, inserts their thumb between the interlocking piece 322 and the accommodating section 320. When the thumb is inserted, the outer edge adhesive section 350 is peeled off from the location where it has been stuck. When the outer edge adhesive section 350 is peeled off, the user rubs the surface of the accommodating section 320 with the palm. With this, the interlocking piece attachment sheet 360 and the cover sheet 362 are mutually subjected to forces in the opposite direction. On receiving the force, the interlocking piece attachment sheet 360 and the cover sheet 362 are subjected to a shearing force. With this, as described above, the interlocking piece attachment sheet 360 and the cover sheet 362 can be peeled off easily at the bonding region 332. The outlet 330 opens when peeled off. Once the outlet 330 is open, the user pushes the edge of the medication 100 through the accommodating section 320. The static friction coefficient of the surfaces inside the accommodating section 320 is less than the static friction coefficient of the surfaces outside the accommodating section 320 in the medication storage cell 12 related to this embodiment. Therefore, the medication 100 can be pushed smoothly towards the outlet 330. The user continues to push the medication 100. As a result, the medication 100 comes out of the accommodating section 320 through the outlet 330. The user takes the medication 100 which comes out of the accommodating section 320.

In addition, the user can hold the knob 352 and pull when peeling off the outer edge adhesive section 350.

[Explanation of the Effect]

The outlet 330 of the accommodating section 320 in the first medication storage cell 312 and the second medication storage cell 314 related to this embodiment is closed by the adhesive region 332 and the bending location 354. Since the outlet 330 is closed by the bending location 354 in addition to the adhesive region 332, the adhesive strength of the adhesive region 332 can be lowered compared to the case where the outlet 330 is closed only by the adhesive region 332. Since the outlet 330 is closed by the bending location 354 in addition to the adhesive region 332, the size of the first medication storage cell 312 and the second medication storage cell 314 can be reduced compared to the case where the outlet 330 is closed only by the adhesive region 332 without bending the outlet sheet section at the bending location 354. As a result, offering a compact first medication storage cell 312 and second medication storage cell 314 from which the medication 100 can be removed easily is possible.

The static friction coefficient of the surface layer 388 is more than the primary barrier layer 380 in the first medication storage cell 312 and the second medication storage cell 314 related to this embodiment. With this, when the user rubs the surface of the accommodating section 320, the frictional force generated in the surface layer 388 is more than the frictional force generated in the primary barrier layer 380. As a result, the medication 100 inside the accommodating section 320 slides well when the user rubs the surface of the accommodating section 320. The medication 100 can be easily pushed out when the user rubs the surface of the accommodating section 320 with the palm because of the ease in sliding.

The primary barrier layer 380 of the first medication storage cell 312 and the second medication storage cell 314 related to this embodiment is made from a fluoropolymer. With this, there is almost no deterioration due to chemical reaction with the medication 100 compared to the use of other synthetic resin materials.

The outer edge section 376 having a curved contour is provided at the corners of the accommodating section 320 of this embodiment. The outer edge section 376 having this curved contour is less likely to cause damage the human body when compared to acute or right angle sections. With this, the accommodating section 320 is less likely to damage the human body when the accommodating section 320 has an outer edge section 376 compared to the case where there is no such outer edge section. Specifically, the possibility of the accommodating section 320 damaging the internal organs of humans when the first medication storage cell 312 or the second medication storage cell 314 is swallowed by mistake is low. Furthermore, it is preferable that even the corners of the interlocking piece 322, or the corners of the bent location 354 of the accommodating section 320 in the state in which the interlocking piece 322 is bonded through the cut out with the outer edge adhesive section 350 (outer edge adhesive section 350 will be described below), namely, the interlocking piece 322 is bent such that the outlet 330 is closed, having a curve contour. With this, the possibility of the outer edge section damaging the internal organs of humans is low.

According to the first medication storage cell 312 and the second medication storage cell 314 related to this embodiment, the cell can be opened by inserting the thumb between the interlocking piece 322 and the accommodating section 320, and then rubbing the interlocking piece attachment sheet 360 and the accommodating section cover sheet 362. The interlocking piece attachment sheet 360 and the cover sheet 362 are bent at the bending location 354. The adhesive strength of the bonding region 332 can be very less since the outlet 330 is closed by this bending. Since the adhesive strength can be very less, persons having little force at their fingertips can easily open the medication storage cell 12 related to this embodiment.

Also, in the first medication storage cell 312 and the second medication storage cell 314 related to this embodiment, the interlocking piece attachment sheet 360 and the cover sheet 362 are mutually pasted at the adhesive region 332. Moreover, the overlapping sheets (the interlocking piece attachment sheet 360 and the cover sheet 362) are bent at the bending location 354. With this, the outlet 330 can be firmly closed while the outer edge adhesive section 350 of the interlocking piece 322 is pasted to the accommodating section 320. Moreover, since the shape of the adhesive region 332 is a straight line, the possibility of centralization of the peeling force required to peel the adhesive region 332 anywhere in that region is less compared to the case where any part of the adhesive region 332 is curved. Since the possibility of centralization of the strength anywhere in the adhesive region 332 is low in addition to closing of the outlet 330, therefore the adhesive strength of the adhesive region 332 can be lowered when compared to the case where the possibility is not low.

Explanation of Alternative Example

The strip packaging body 10, 310, the small medication storage cell 12, the large medication storage cell 14, the first medication storage cell 312 and the second medication storage cell 314 described above are the embodiment of the technical idea of this invention. These are obtained by adding various changes within the scope of the technical idea of this invention.

For example, the shape of the outlet region 32 is not limited to a straight line shape in the small medication storage cell 12, the large medication storage cell 14 and the medication storage cell 18. For example, any location of the outlet region 32 may be curved. The outlet region 32 need not be bonded.

Also, the shape of the interlocking piece 22 is not limited to those described above. For example, the thickness of the tip end section 42 can be equal to or greater than the thickness of the base section 40. Also, the interlocking piece 22 can have the shape of the well-known spoon part where things are placed.

Also, the materials of the interlocking piece attachment sheet 60 and the cover sheet 62 can be well-known soft synthetic resins sheets that have been subject to some kind of surface treatment. The surface treatment can consist of multiple layers. The inner surfaces of the accommodating section may be provided with uneven surfaces. With this, ease of taking out the removing medication 100 can be set arbitrarily.

Also, perforations need not be formed in the strip packaging body 10. In this case, the small medication storage cell 12 and the large medication storage cell 14 can be cut off using any of the instrument such as scissors.

Also, there is no particular restriction on the number of rows of medication storage cells to be provided in the strip packaging body 10. The number of rows may be 1 or may be 3 or more rows. Accordingly, the number of rows of the medication 100 formed in the medication arrangement process S220 is also not particularly limited.

Also, the locations which can be bent in the small medication storage cell 12, and the large medication storage cell 14 are not limited to the bending location 52 that have been described above. For example, the location can be within the outlet region 32. This is the same for the first medication storage cell 312, and the second medication storage cell 314.

Also, the structure of the cover forming body 112 is not limited to those described above. For example, the adhesive layer can be provided on the entire surface of the base layer 140. In this case, the difference in the adhesive strength of the outlet region 32, and the adhesive strength in the edge region 34 and the bottom region 36 may be achieved by the difference in the pressing time of the heating unit in the strong bonding process S230 and the pressing time of the heating unit in the weak bonding process S232.

Also, a part of the base section 40 can be bonded to the surface of the accommodating section 20. A part of the base section 40 can be stuck to the surface of the accommodating section 20. That is, separating at least a part of the base section 40 from the surface of the accommodating section 20 is all right. Also, there is no particular limit on the size of the tip adhesive section 50. That is, there is no limit on the area of the tip end section 42 total area bonding to the surface of the accommodating section 20.

Also, the holding method for the tip end section 42 of the interlocking piece 22 for the accommodating section 20 is not limited to the adhesive. For example, the tip end section 42 of the interlocking piece 22 can be stuck to the surface of the accommodating section 20. The tip end section 42 of the interlocking piece 22 can be held at the surface of the accommodating section 20 by using well-known materials that are used to stick one object to another. The tip end section 42 of the interlocking piece 22 may be inserted into a cut provided at the accommodating section 20. If the tip end section 42 of the interlocking piece 22 is inserted into the cut provided in the accommodating section 20, there is no limit on the position and size of the cut. However, providing the cut in the edge region 34 or the bottom region 36 is preferable. With this, the connection between the space accommodating the medication 100 of the accommodating section 20 and the space around the accommodating section 20 can be prevented.

Also, the medication storage cell related to this invention may be provided with a sheet restraining section that is different with from the one described above. Namely, although a part of the sheet described above is restrained such that the bent condition is maintained to close the outlet 30, 330, the embodiment is not particularly limited to the interlocking piece 22, 322 described above. Furthermore, the sheet restraining section refers to those that restrain the part of the overlapping sheets configuring the outlet 30, 330. The sheet restraining section may or may not be integrated with those sheets. There are no particular limitations on the configuration of the sheet restraining section. May consist only of the interlocking piece described above, or may consist of the interlocking piece and other parts. The sheet restraining section may consist of a part that is different from the interlocking piece. A specific example of the sheet restraining section is an adhesive tape.

Also, the medication storage cell related to this invention may be provided with a limiting section that is different from the one described above. Namely, the particular embodiment of the restriction for the movable range of the medication 100 within the accommodating section 320 is not limited to that described above.

Also, the medication storage cell related to this invention is not limited to the accommodating section formed by the bonding of two sheets. For example, the accommodating section may be formed by a single sheet which has been valley folded.

Figure 15:
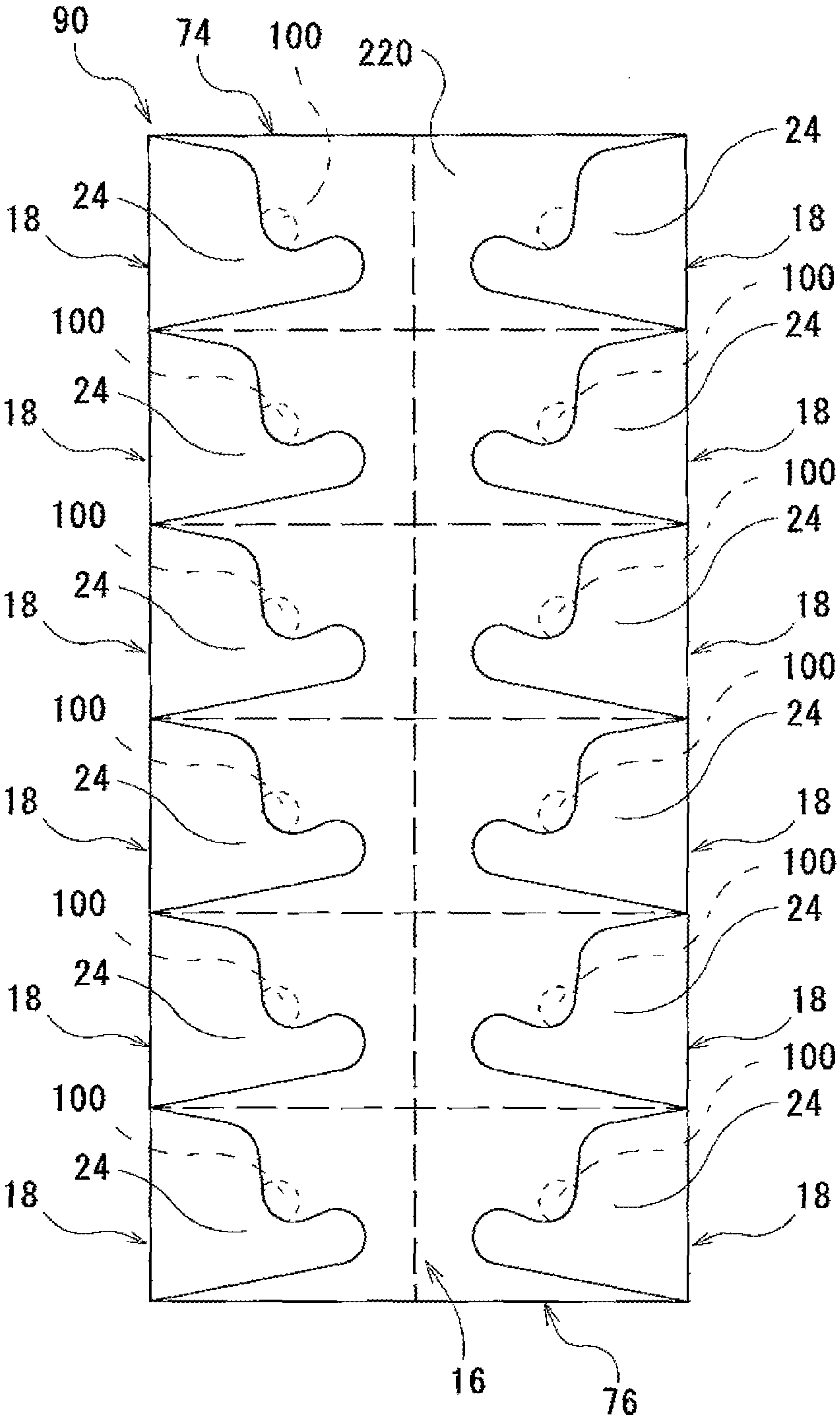
FIG. 15 Plan view of the strip packaging body related to the alternative example of this invention.

FIG. 15 is the plan view of the strip packaging body 90 related to an alternative example of this embodiment described above. The strip packaging body 90 related to this alternative example is provided with multiple numbers of the medication storage cell 12 and the bending section between rows 16.

Any of the medication storage cell 18 is intended to accommodate the medication 100. The structure of the medication storage cell 18 is identical to the structure of the small medication storage cell 12 described above except for the differences mentioned below. The differences are, shape of the interlocking piece 24 is different, and all the bending section between rows 16 is covered by the cover forming body 220. As apparent from FIG. 15, several of the medication storage cell 18 is lined up to configure the first row 74. The other medication storage cell 18 is lined up to configure the second row 76. The bending section between rows 16 is provided between the first row 74 and the second row 76. The strip packaging body 90 related to this alternative example can be bent at the bending section between rows 16.

In this alternative example as apparent from FIG. 15, the medication storage cell 18 configuring the first row 74 lines up facing the medication storage cell 18 configuring the second row 76 when the strip packaging body 90 is bent at the bending section between rows 16. The medication storage cell 18 configuring the second row 76 lines up facing the medication storage cell 18 configuring the first row 74 when the strip packaging body 90 is bent at the bending section between rows 16.

Also, the particular configuration of the devices to realize each process of the manufacturing method of the strip packaging body related to this invention is not limited to those described above. Moreover, each of the processes may be performed by a person.

Also, the interlocking piece forming process S204 may be implemented before (for example, immediately before the medication arrangement process S220) the covering process S222. In this case, clipping the boundary section 80 of two numbers of the small medication storage cell 12 and the boundary section 82 of two numbers of the large medication storage cell 14 of the interlocking piece forming sheet 110 is preferable. In this case, preferably the cover forming body 112 must not be clipped. In this case, the locations which are bent in the bending process S206, are preferably near the edge of the cover forming body 112 of the interlocking piece forming sheet 110 region. If the interlocking piece forming process S204 is implemented just before the medication arrangement process S220, then the interlocking piece 22 can be formed without affecting the medication 100. The interlocking piece forming process S204 can be implemented after the weak bonding process S232 and before the bending process S206. The interlocking piece forming process S204 need not be implemented.

Also, in the accommodation bonding process S200, the specific procedure to accommodate the medication 100 between the interlocking piece forming sheet 110 and the cover forming body 112, and, to bond the surrounding region of the medication 100 such that the outlet 30 is formed is not limited to those described above. For example, the medication 100 can be inserted between the interlocking piece forming sheet 110 and the cover forming body 112 after the region corresponding to the edge region 34 and the bottom region 36 of the surrounding region are bonded.

In the medication arrangement process S220, the medication 100 may be arranged on the surface of the interlocking piece forming sheet 110, and there are no particular limitations on the specific tools.

Also, the strong bonding process S230, and the weak bonding process S232 may be carried out simultaneously. These may be performed sequentially. Namely, the strong bonding process S230 and the weak bonding process S232 having the periphery bonding process S224 is only preferable. Also, implementing the strong bonding process S230 at the locations where the covering process S222 has been implemented following the covering process S222 is only preferable. The perforation forming process S202 can be implemented after the weak bonding process S232.

Also, the medication storage cell related to this invention can be manufactured one at a time. In this case, for example, the medication, the interlocking piece forming sheet of size for 1 medication storage cell, and the cover forming body of size for 1 medication storage cell can be used as the material.

Also, the number of medications that can be placed in one medication storage cell related to this invention is not limited to one. That number may be two or more. For example, tablets that are to be taken at one time may be placed in the accommodating section.

Also, the medication storage cell related to this invention, may be provided with a X-ray opaque portion. There is no particular limit on the embodiment of the X-ray opaque portion. For example, the shape may be a line. The X-ray opaque portion can be formed by bonding or printing materials containing barium. The location of the medication storage cell can be easily detected when swallowed by mistake with the provision of the X ray opaque portion.

Note that, this invention is not limited to the above-mentioned embodiments. Although it is to those skilled in the art, the following are disclosed as the one embodiment of this invention.

- Mutually substitutable members, configurations, etc. disclosed in the embodiment can be used with their combination altered appropriately.
- Although not disclosed in the embodiment, members, configurations, etc. that belong to the known technology and can be substituted with the members, the configurations, etc. disclosed in the embodiment can be appropriately substituted or are used by altering their combination.
- Although not disclosed in the embodiment, members, configurations, etc. that those skilled in the art can consider as substitutions of the members, the configurations, etc. disclosed in the embodiment are substituted with the above mentioned appropriately or are used by altering its combination.

While the invention has been particularly shown and described with respect to preferred embodiments thereof, it should be understood by those skilled in the art that the foregoing and other changes in form and detail may be made therein without departing from the sprit and scope of the invention as defined in the appended claims.

EXPLANATION OF THE REFERENCES

10, 90, 310: Strip packaging body
12: Small medication storage cell
14: Large medication storage cell
16: Bending section between rows
18: Medication storage cell
20, 320: Accommodating section
22, 24, 322: Interlocking piece
30, 330: Outlet
32: Outlet region
34, 334: Edge region
36, 336: Bottom region
40: Base section
42: Tip section
50: Tip adhesive section
52, 354: Bending location
60, 360: Interlocking piece attachment sheet.
62, 362: Cover sheet
70, 74: First row
72, 76: Second row
80, 82: Boundary section
100: Medication
110: Interlocking piece forming sheet.
112,220: Cover forming body
120: Robot
130: Suction unit
132: Moving unit
140: Base layer
142: Adhesive layer
150: Weak adhesive region
152: Strong adhesive region
160: Interlocking part
312: First medication storage cell
314: Second medication storage cell
316: Connecting section
324: Label section
332: Adhesive region
340: Cut out
342: Limiting unit
350: Outer edge adhesive section
352: Knob section
376: Outer edge section
380: Primary barrier layer
382: Sealant layer
384: Adhesive layer
386: Secondary barrier layer
388: Surface layer
400: Strip packaging body manufacturing system
410: First material sheet drawing device
412: First guide roller
414: Second material sheet drawing device
416: Second guide roller
418: Cut out forming roller unit
420: Tablet supply unit
422: Vertical bonding roller unit
424: Horizontal bonding roller unit
426: Perforations forming roller unit
428: Heating device
430: Bending guide unit
432: Press roller unit
434: Facing location bonding roller unit
436: Cutting roller unit
510: Interlocking piece forming sheet
512: Cover forming body

What is claimed is:

1. A medication storage cell, provided with an accommodating section to accommodate a medication;

the said accommodating section has an outlet for the said medication;

the said outlet is formed by two overlapping sheets;

the said two overlapping sheets are bent such that the said outlet is closed;

provided with a sheet restraining section restraining a part of the said two overlapping sheets to maintain the bent state such that the said outlet is closed;

the said sheet restraining section is provided with an interlocking piece on one of the said two overlapping sheets;

the said two overlapping sheets are bonded to each other around the said medication at an adhesive region, an edge region and a bottom region accommodating the said medication between the said two overlapping sheets;

the said outlet is closed by the said adhesive region;

an adhesive strength of the said two overlapping sheets is lower at the said adhesive region compared to the said edge region and the said bottom region; and the said interlocking piece is held at one of the said two overlapping sheets through the cut out provided on the other of the said two overlapping sheets.

2. The medication storage cell defined in claim 1, wherein;

the bent locations of the said two overlapping sheets are arranged between the said medication and the said adhesive region.

3. The medication storage cell defined in claim 1, wherein;

the bent locations of the said two overlapping sheets are arranged at the said adhesive region.

4. The medication storage cell defined in claim 1, wherein the said two overlapping sheets are bonded to each other at a limiting section to restrict a movable range of the said medication.

5. The medication storage cell defined in claim 1, wherein a friction coefficient of the inner surface of the said accommodating section that comes in contact with the said medication is lower than a friction coefficient of the outer surface.

* * * * *